US010017762B2

(12) United States Patent
Rivera et al.

(10) Patent No.: US 10,017,762 B2
(45) Date of Patent: *Jul. 10, 2018

(54) COMPOSITIONS AND METHODS FOR TREATING OR PREVENTING LUPUS

(71) Applicant: The United States of America, as represented by the Secretary, Department of Health & Human Services, Washington, DC (US)

(72) Inventors: Juan Rivera, Mechanicsburg, PA (US); Nicolas Charles, Asnieres sur Seine (FR)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/498,202

(22) Filed: Apr. 26, 2017

(65) Prior Publication Data

US 2017/0275617 A1 Sep. 28, 2017

Related U.S. Application Data

(63) Continuation of application No. 13/989,744, filed as application No. PCT/US2010/058077 on Nov. 24, 2010, now Pat. No. 9,657,292.

(51) Int. Cl.
*A61K 39/395* (2006.01)
*C12N 15/11* (2006.01)
*C07K 16/28* (2006.01)
*A61K 31/5383* (2006.01)
*C07K 16/42* (2006.01)
*A61K 31/675* (2006.01)
*A61K 45/06* (2006.01)
*A61K 31/519* (2006.01)
*A61K 31/5377* (2006.01)

(52) U.S. Cl.
CPC ............ *C12N 15/11* (2013.01); *A61K 31/519* (2013.01); *A61K 31/5377* (2013.01); *A61K 31/5383* (2013.01); *A61K 31/675* (2013.01); *A61K 39/395* (2013.01); *A61K 39/39533* (2013.01); *A61K 39/39566* (2013.01); *A61K 45/06* (2013.01); *C07K 16/2803* (2013.01); *C07K 16/4291* (2013.01)

(58) Field of Classification Search
None
See application file for complete search history.

(56) References Cited

U.S. PATENT DOCUMENTS

| 5,874,082 | A | | 2/1999 | De Boer | |
|---|---|---|---|---|---|
| 6,072,035 | A | * | 6/2000 | Hardman | ............ C07K 16/4291 424/133.1 |
| 6,267,958 | B1 | | 7/2001 | Andya et al. | |
| 6,627,195 | B1 | * | 9/2003 | Paul | ...................... C07K 14/005 424/133.1 |
| 6,732,833 | B2 | * | 5/2004 | Rogelja | ..................... A62B 1/14 182/193 |
| 7,867,494 | B2 | * | 1/2011 | Liu | ..................... C07K 16/4291 424/133.1 |
| 7,959,917 | B2 | * | 6/2011 | Cochrane | ................ C07K 16/26 424/133.1 |
| 8,071,097 | B2 | * | 12/2011 | Wu | ..................... A01K 67/0278 424/133.1 |
| 8,435,517 | B2 | * | 5/2013 | Desjarlais | ........... C07K 16/4291 424/133.1 |
| 8,460,664 | B2 | * | 6/2013 | Chang | ................ C07K 16/4291 424/133.1 |
| 9,617,348 | B2 | * | 4/2017 | Desjarlais | ........... C07K 16/4291 |
| 9,657,292 | B2 | * | 5/2017 | Rivera | ................... A61K 45/06 |
| 9,718,891 | B2 | * | 8/2017 | Chang | ................ C07K 16/4291 |
| 9,850,317 | B2 | * | 12/2017 | Ohara | ................ C07K 16/4291 |
| 2003/0077282 | A1 | * | 4/2003 | Bigler | ................ C07K 16/2803 424/144.1 |
| 2005/0054614 | A1 | | 3/2005 | Diacovo et al. | |
| 2005/0158303 | A1 | | 7/2005 | Liu | |
| 2006/0073142 | A1 | | 4/2006 | Chan | |
| 2006/0263349 | A1 | | 11/2006 | McCutcheon et al. | |
| 2008/0081788 | A1 | | 4/2008 | Lipps | |
| 2008/0260737 | A1 | | 10/2008 | Ponce et al. | |

FOREIGN PATENT DOCUMENTS

| JP | H9-511757 | | 11/1997 | |
|---|---|---|---|---|
| WO | WO 1996/012741 | | 5/1996 | |
| WO | WO 2007/032804 | | 3/2007 | |
| WO | WO 2007/095230 | | 8/2007 | |
| WO | WO 2007095230 | A2 * | 8/2007 | ......... C07K 16/2803 |
| WO | WO 2010/097248 | | 9/2010 | |

OTHER PUBLICATIONS

Wright et al., Sci Rep. Jun. 26, 2015;5:11581. doi: 10.1038/srep11581.*
Trotter et al., Curr Opin Rheumatol. Sep. 2016;28(5):460-7.*
Charles et al., Nat Med. Jun. 2010;16(6):701-7. doi: 10.1038/nm.2159. Epub May 30, 2010.*
American College of Rheumatology, Arthritis Rheum. 50, 3418-3426, 2004.
Akahoshi, M. et al. (1999) Arthritis Rheum. 42, 1644-1648.
Asai, K. et al. (2001) Immunity 14, 791-800.
Atta, "Immunoglobulin E and systemic lupus erythematosus", Brazilian Jounal of Medical and Biological Research, 2004, vol. 37, No. 10, p. 1497-1501.
Bahjat, "An orally bioavailable spleen tyrosine kinase inhibitor delays disease progression and prolongs survival in murine lupus", Arthritis and Rheumatism, 2008, vol. 58, No. 5, p. 1433-1444.

(Continued)

*Primary Examiner* — Michael Szperka
(74) *Attorney, Agent, or Firm* — Bryan D. Zerhusen; Locke Lord LLP

(57) ABSTRACT

The present disclosure provides methods for inhibiting and/or reducing self-reactive IgE and/or basophils, thereby treating or preventing lupus, lupus nephritis, and lupus-related disorders.

10 Claims, 29 Drawing Sheets

(56) References Cited

OTHER PUBLICATIONS

Balomenos, D. et al., (1998) J. Clin. Invest. 101, 364-371.
Beavitt, S.J. et al. (2005) J. Immunol. 175, 1867-1875.
Burmeister Getz et al. (2009) J. Clin. Pharmacol. 49, 1025-1036.
Busse and Neaville, 2001 Curr Opin Allergy Clin Immuno 1(1):105-108.
Charles, "Basophils and the T Helper 2 Environmental Can Promote the Development of Lupus Nephritis", Nature Medicine, Jun. 2010, vol. 16, No. 6, p. 701-707.
Charles, "Lyn Kinase Controls Basophil Gata-3 Transcription Factor Expression and Induction of Th2 Cell Differentiation", Immunity, 2009, vol. 30, No. 4, p. 533-543.
Chen, K. et al. (2009) Nat. Immunol. 10, 889-898.
Corren et al., 2003 J Allergy Clin Immuno 111(1):87-90.
De Carli, M. et al. (1994) Autoimmunity 18, 301-308.
Deng, "Suppression of Skin and Kidney Disease by Inhibition of Spleen Tyrosine Kinase in Lupus-Prone Mice", Arthritis and Rheumatism, Jul. 2010, vol. 62, No. 7, p. 2086-2092.
Denzel, A. et al. (2008) Nat. Immunol. 9, 733-742.
Egido, "Evidence of an Immediate Hypersensitivity Mechanism in Systemic Lupus Erythematosus", Annals of the rheumatic Diseases, 1980, vol. 39, No. 4, p. 312-317.
Enyedy, "Fce Receptor Type I & Chaim Replaces the Deficient T Cell Receptor Chain in T Cells of Patients with Systemic Lupus Erythematosus", Arthritis and rheumatism, 2001, vol. 44, No. 5, p. 1114-1121.
Finn et al., 2003 J Allergy Clin Immuno 111(2):278-284.
Hauswirth, A.W. et al. (2002) J. Allergy Clin. Immunol. 110, 102-109.
Heine, G. et al. (2002) Nephrol. Dial. Transplant. 17, 1790-1794.
Hibbs, M.L. et al. (1995) Cell 83, 301-311.
Hochberg, M.C. (1997) Arthritis Rheum. 40, 1725.
Holgate et al., Curr Med Res Opin. 2001;17:233-240.
Holmdahl, R. et al. (1991) Autoimmunity 8, 271-280.
Johansson et al., Ann Allergy Asthma Immunol. 2002;89:132-138.
Kalesnikoff, J. et al. (2001) Immunity 14, 801-811.
Kaplan, "Treatment of chronic autoimmune urticarial with omalizumab", The Journal of Allergy and Clinical Immunology, 2008, vol. 122, No. 3, p. 569-573.
Kono, D.H. et al. (2000) Journal of Immunol. 164, 38-42.
Kopf, M. et al. (1993) Nature 362, 245-248.
Kyttaris, V.C. et al. (2005) Curr. Rheumatol. Rep. 7, 469-475.
Lee, H.Y. et al. (2008) Rheumatology (Oxford) 47, 789-794.
Levesque, M.C. (2009) Clin. Exp. Immunol. 157, 198-208.
Lin, H. et al. (2004) J. Allergy Clin. Immunol. 113, 297-302.
Liossis, S.N. et al. (2001) J. Investig. Med. 49, 157-165.
Liu, F.T. et al. (1980) J. Immunol. 124, 2728-2737.
Lu, R. et al. (2009) Genes Immun. 10, 397-403.
Masutani, K. et al. (2001) Arthritis Rheum. 44, 2097-2106.
Moser, K.L. et al., (2009) Genes Immun. 10, 373-379.
Mukai, K. et al. (2005) Immunity 23, 191-202.
Nalbandian, A. et al. (2009) Clin. Exp. Immunol. 157, 209-215.
Nishizumi, H. et al. (1995) Immunity 3, 549-560.
Odom, S. et al. (2004) J. Exp. Med. 199, 1491-1502.
Oettgen, H.C. et al. (1994) Nature 370, 367-370.
Peng, S.L. et al. (1997) J. Clin. Invest. 99, 1936-1946.
Peng, S.L. et al., (2002) Proc. Natl. Acad. Sci. USA 99, 5545-5550.
Pernis, A.B., (2009) J. Intern. Med. 265, 644-652.
Perrigoue, J.G. et al. (2009) Nat. Immunol. 10, 697-705.
Rahman, A. & Isenberg, D.A., (2008) N. Engl. J. Med. 358, 929-939.
Schroeder, J.T. & MacGlashan, D.W. (1997) J. Allergy Clin. Immunol. 99, 429-433.
Seshan, S.V. & Jennette, J.C. (2009) Arch. Pathol. Lab. Med. 133, 233-248.
Shimizu, S. et al. (2005) J. Immunol. 175, 7185 7192.
Singh, R.R. et al. (1995) J. Clin. Invest. 96, 2990-2996.
Sinico, R.A. et al. (2009) Ann. NY Acad. Sci. 1173, 47-51.
Sokol, C.L. et al. (2009) Nat. Immunol. 10, 713-720.
Sokol, C.L. et al. (2008) Nat. Immunol. 9, 310-318.
Tan, E.M. et al. (1982) Arthritis Rheum. 25, 1271-1277.
Tang and Powell, 2001, Eur J Pediatr 160(12): 696-704.
Tiller, T. et al. (2007) Immunity 26, 205-213.
Toran, E.J. & Lee, C.M. (1995) J. Natl. Med. Assoc. 87, 693-699.
Tsuiji, M. et al. (2006) J. Exp. Med. 203, 393-400.
Valencia, X. et al. (2007) J. Immunol. 178, 2579-2588.
Yoshimoto, T. et al. (2009) Nat. Immunol. 10, 706-712.
Yu, C.C. et al. (2001) Curr. Biol. 11, 34-38.
Zeng, D. et al., (2003) J. Clin. Invest. 112, 1211-1222.
Zhao, X.F. et al. (2010) Mol. Biol. Rep. 37, 81-85.
J. C. Crispín, S. N. C. Liossis, K. Kis-Toth et al., "Pathogenesis of human systemic lupus erythematosus: recent advances," Trends in Molecular Medicine, vol. 16, No. 2, pp. 47-57, 2010.
International Preliminary Report on Patentability for corresponding International Application Serial No. PCT/US2010/058077, dated May 28, 2013.
Trotter, et al., Curr Opin Rheumatol. Sep. 2016:28(5):460-7.
The Merck Manual of Dagnosis and Therapy, 17th edition, 1999, editors Beers and Berkow, Merk Research Laboratories, pp. 426-431.
Holgate, et al., J. Allergy Clin. Immunol. Mar. 2005: 115(3): 459-65.

* cited by examiner

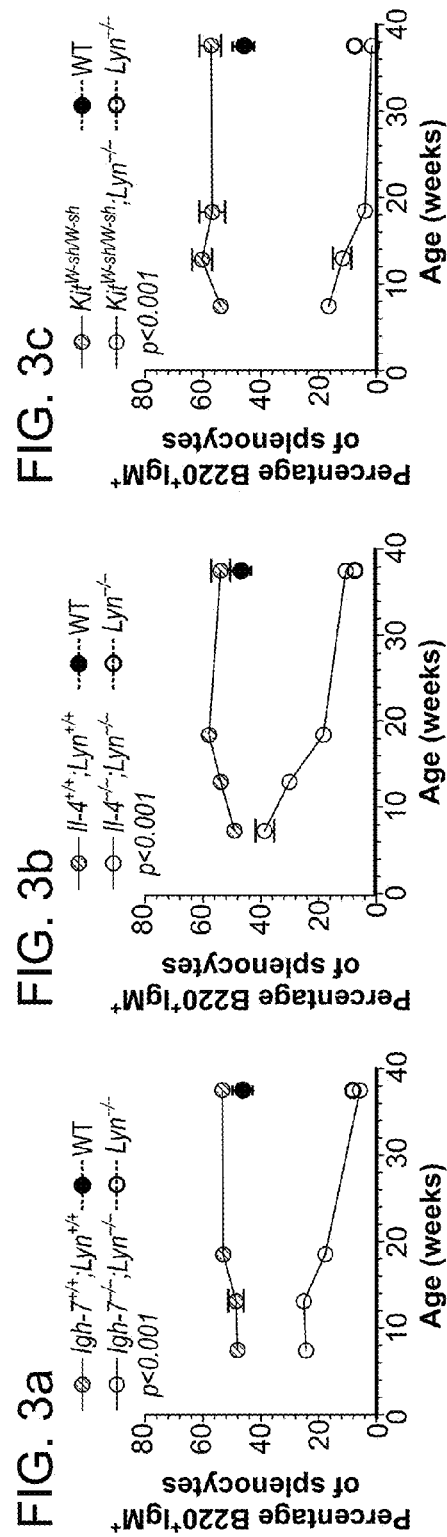
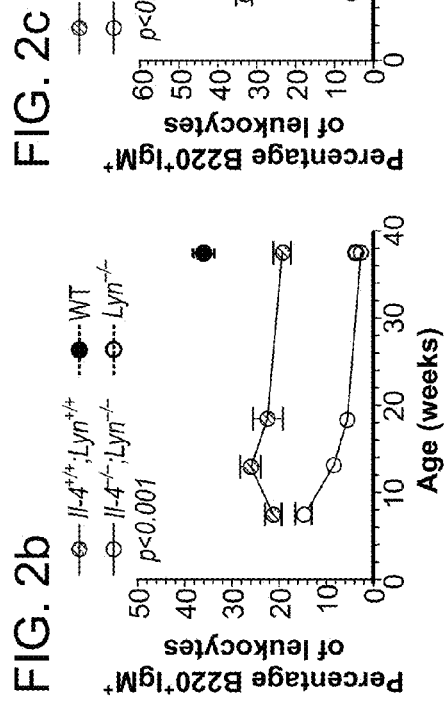
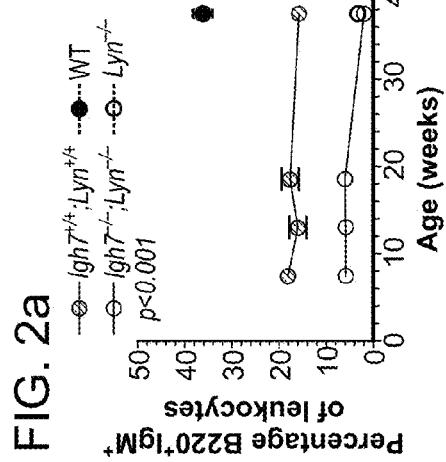

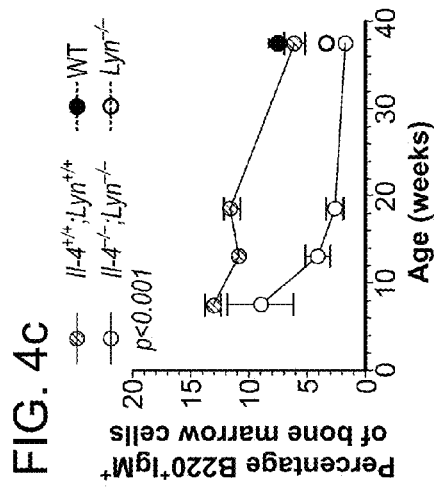
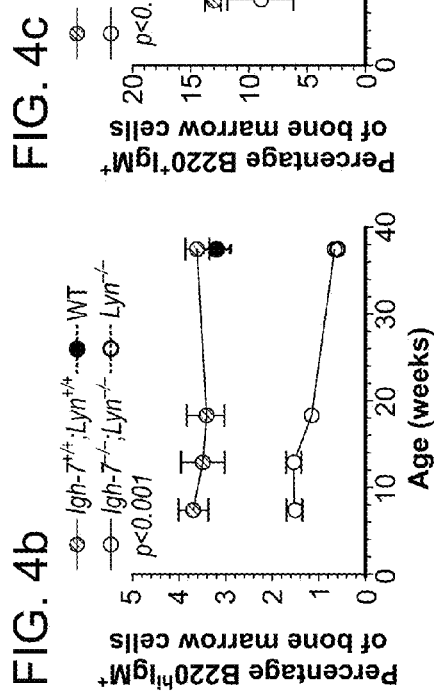
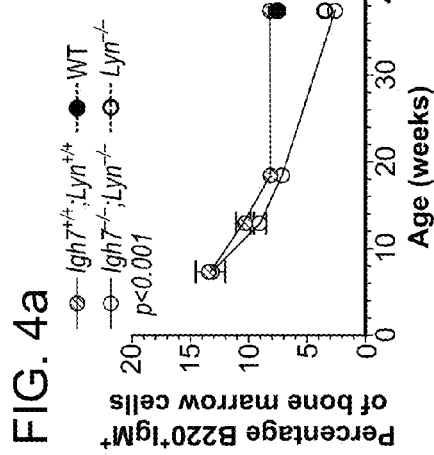
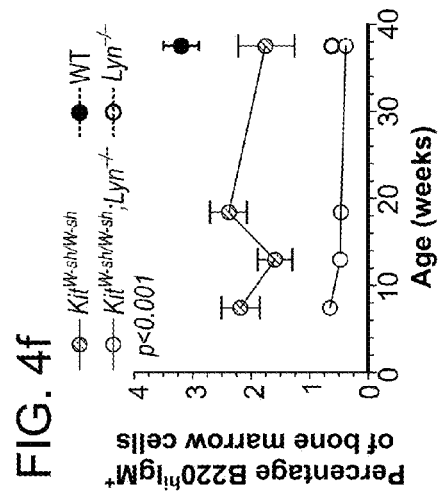
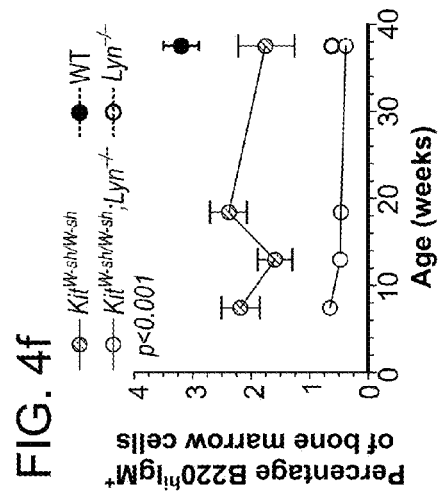
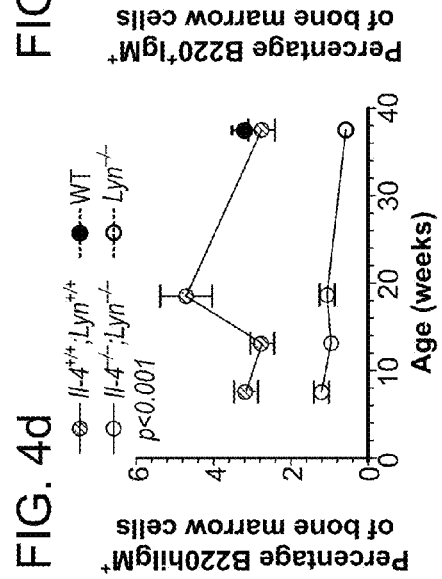

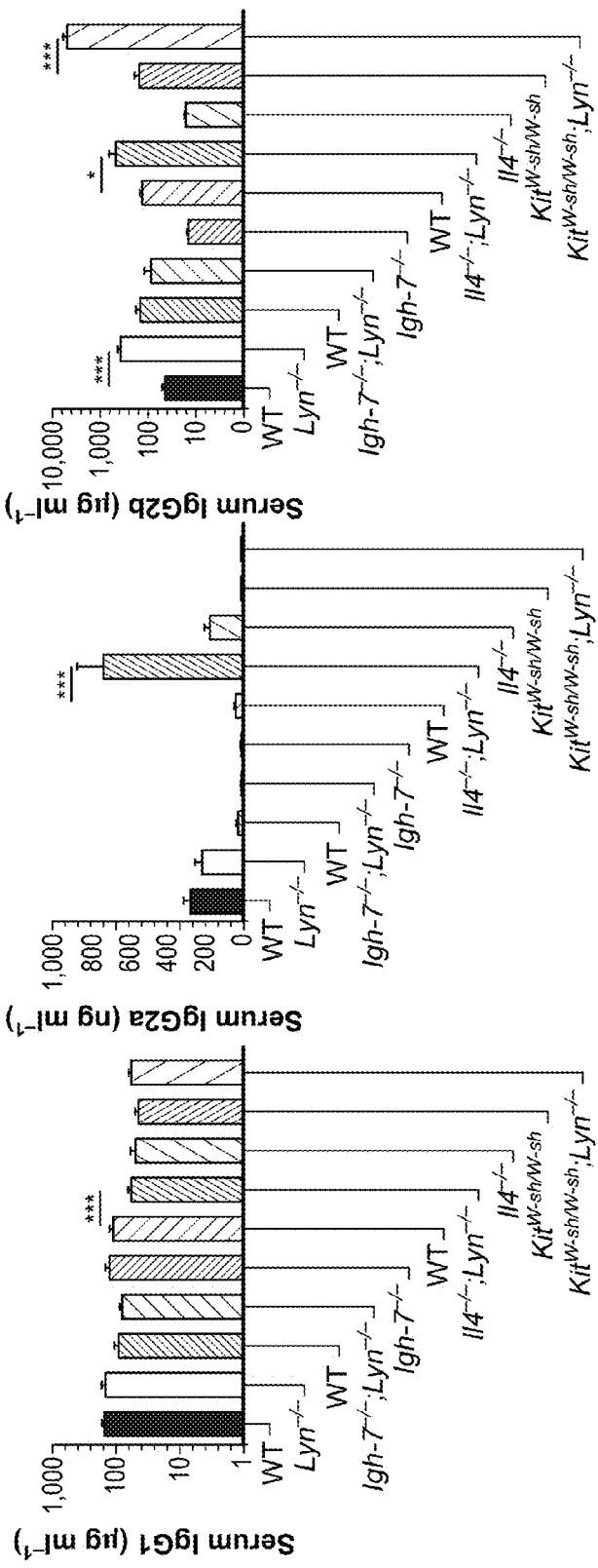

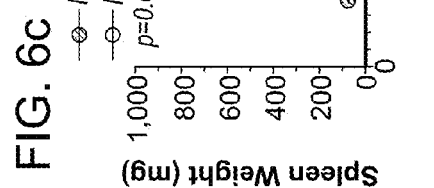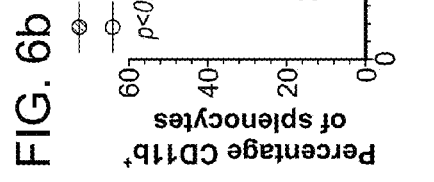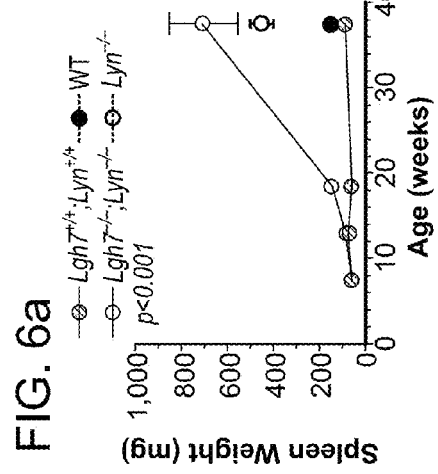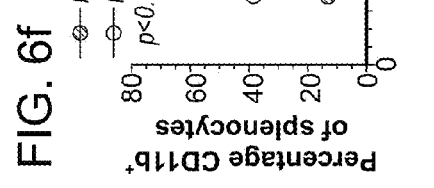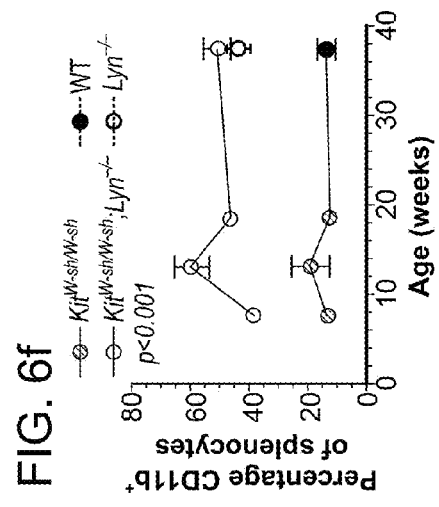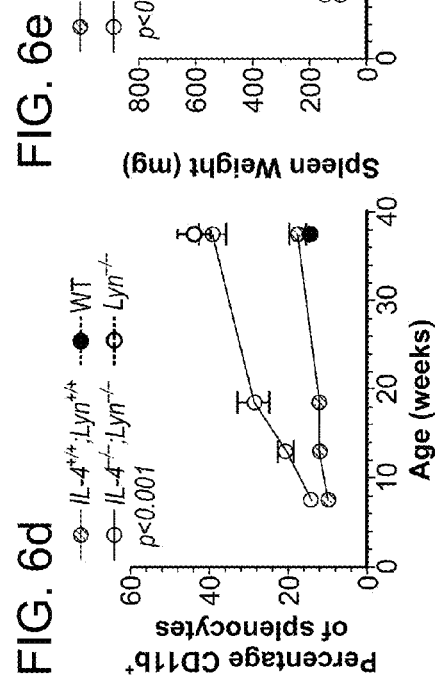

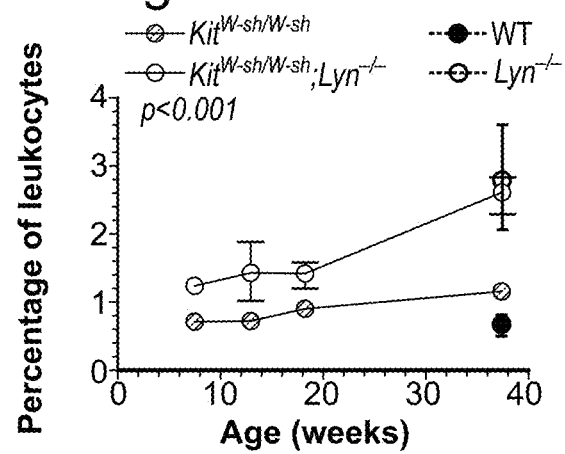

IgM

IgA

C3

IL-12p40

IFN-γ

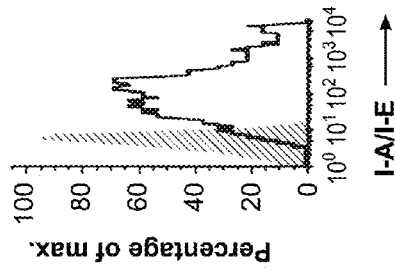
FIG. 16e
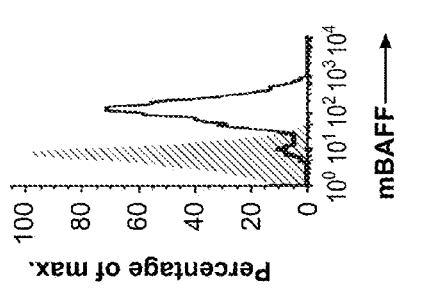
FIG. 16f  FIG. 16g
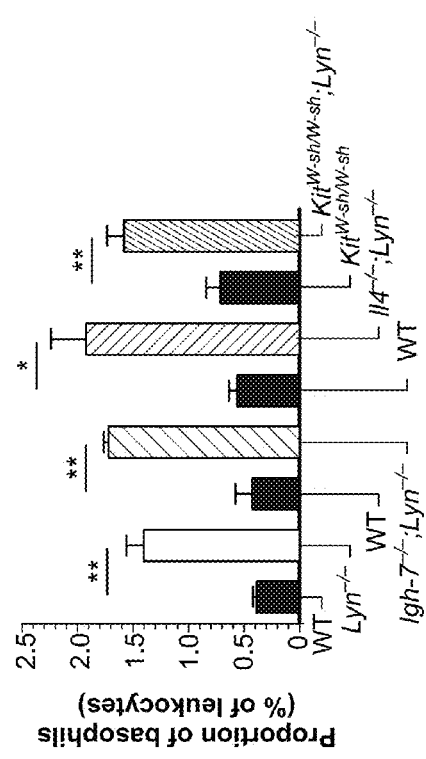
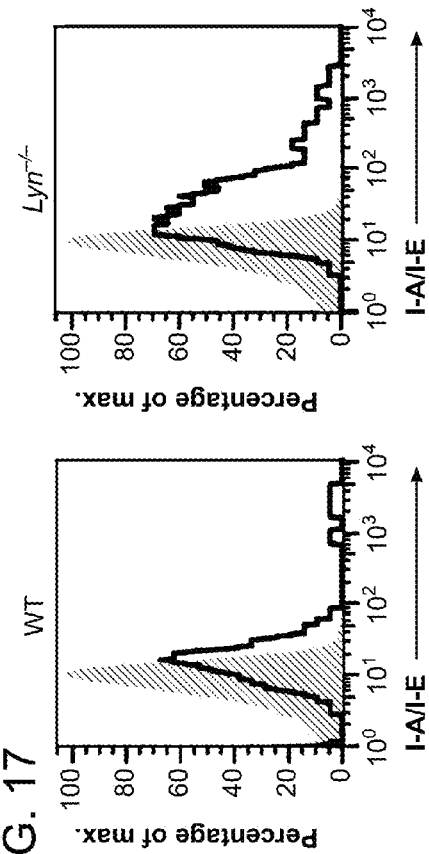
FIG. 17

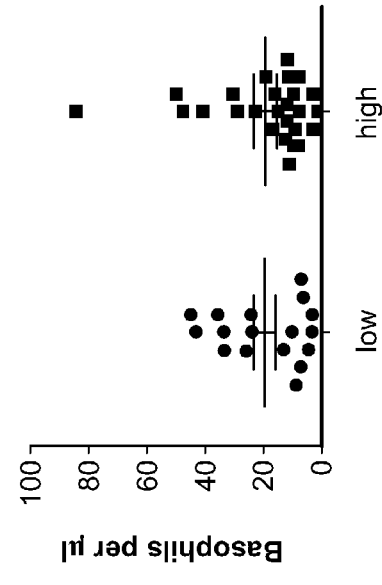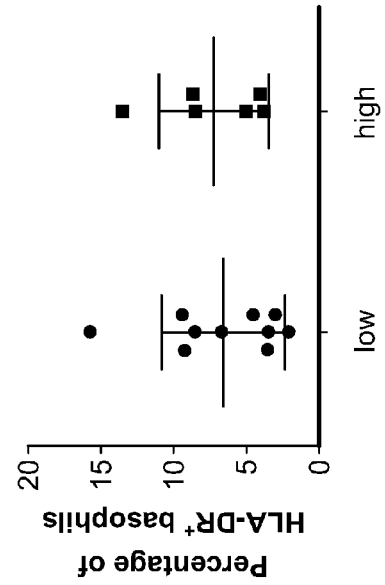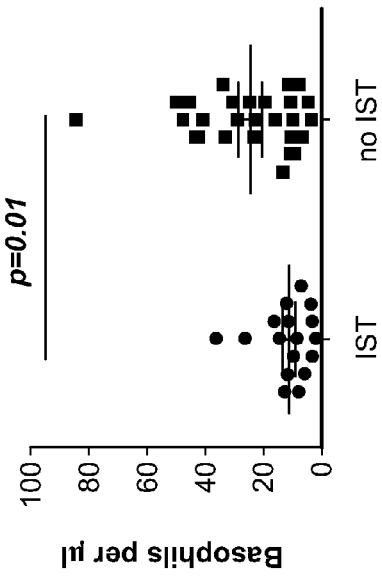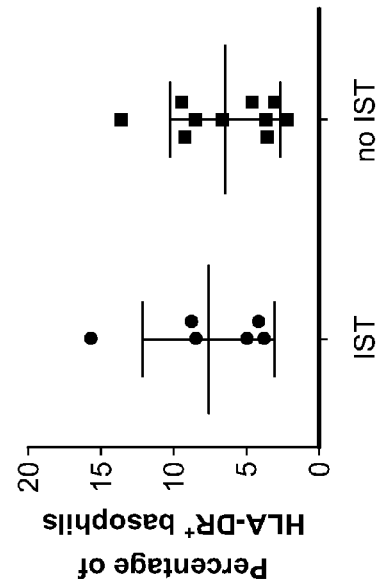
FIG. 21a
FIG. 21b
FIG. 21c
FIG. 21d

FIG. 22

| | |
|---|---|
| Age (Mean, SD) | 38.5±12.9 years |
| Gender (F/M, n,%) | 39 (93%) / 3 (7%) |
| Ethnicity (n, %)<br>    Caucasian<br>    African American<br>    Hispanic<br>    Asian | <br>14 (33.3%)<br>10 (23.8%)<br>12 (28.6%)<br>6 (14.3%) |
| Disease duration (Mean, SD, years) | 12.9±10.8 |
| Anti-dsDNA Ab positive (n,%) | 33 (55%) |
| SLEDAI<br>    Mean, SD<br>    Median, (minimum, maximum) | <br>4.57±5.5<br>4.0 (0, 24) |
| Current prednisone dose (mg/day)<br>    Mean, SD<br>    Median, (minimum, maximum) | <br>12.6±14.9<br>7.5 (0, 60) |
| Concurrent immunosuppressive therapy (n, %)<br>    hydroxychloroquine<br>    mycophenolate mofetil<br>    cyclophosphamide<br>    azathioprine | <br>35 (83%)<br>4 (9.5%)<br>3 (7%)<br>7 (17%) |

FIG. 23

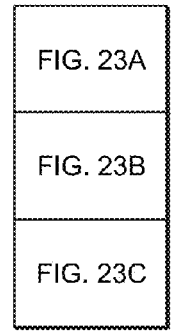

FIG. 23A

| Application | Used in Figure # | Description | Conjugate | Clone | Company |
|---|---|---|---|---|---|
| Basophil depletion | 2, S1 | Hamster, anti-mouse FcεRIα | - | MAR-1 | eBioscience |
| Basophil depletion (isotype control) | 2, S1 | Armenian Hamster IgG | - | eBio299Arm | eBioscience |
| ELISA | 5 | Human IgE | - | HE1 | Abbiotec |
| ELISA | 5, S14 | Mouse anti-human IgE | HRP | ? | ICL |
| ELISA | 5 | Donkey anti-human IgG, Fcγ Specific | HRP | Polyclonal | Jackson IRL |
| ELISA | 3 | Rat anti-mouse IgE | HRP | 23G3 | Southern Biotech |
| ELISA | S14 | Mouse anti-human IgG1 | HRP | HP6070 | Invitrogen |
| ELISA | S14 | Mouse anti-human IgG2 | HRP | HP6014 | Invitrogen |
| ELISA | S14 | Mouse anti-human IgG3 | HRP | HP6049 | Invitrogen |
| ELISA | S14 | Mouse anti-human IgG4 | HRP | HP6023 | Invitrogen |
| Flow cytometry | 4, S1, S7 | Rat anti-mouse CD117 (c-Kit) | APC | 2B8 | BD Biosciences |
| Flow cytometry | S13 | Rat anti-mouse CD117 (c-Kit) | PE-Cy5 | 2B8 | BioLegend |
| Flow cytometry | S1 | Rat anti-mouse CD4 | PerCP-Cy5.5 | RM4-5 | BD Biosciences |
| Flow cytometry | 4 | Rat anti-mouse CD62L | APC | MEL-14 | BD Biosciences |
| Flow cytometry | S1 | Rat anti-mouse interferon gamma | APC | XMG1.2 | BD Biosciences |
| Flow cytometry | S2, S3, S4 | Rat anti-mouse CD45R/B220 | APC | RA3-6B2 | BioLegend |
| Flow cytometry | 6, S15 | Mouse anti-human CD203c | PE | E-NPP3 | BioLegend |
| Flow cytometry | 6, S15 | Mouse anti-human FcεRI alpha | FITC | CRA1 | BioLegend |
| Flow cytometry | 6, S15 | Mouse anti-human CD123 | PerCP-Cy5.5 | 6H6 | BioLegend |
| Flow cytometry | 6, S15 | Mouse anti-human CD117 (c-Kit) | APC | 104D2 | BioLegend |
| Flow cytometry | 6, S15 | Mouse anti-human CD11b | APC | ICRF44 | BioLegend |
| Flow cytometry | 6 | Mouse anti-human CD62L | APC | DREG-56 | BioLegend |
| Flow cytometry | 6, S15 | Mouse anti-human HLA-DR | PerCP-Cy5.5 | L243 | BioLegend |
| Flow cytometry | S12 | Rat anti-mouse IFN-γ | PE | XMG1.2 | BioLegend |
| Flow cytometry | 3, S1 | Rat anti-mouse interlukin-4 (IL-4) | PE | 11B11 | BioLegend |
| Flow cytometry | 3, 4, S1, S7, S12, S13 | Rat anti-mouse CD49b/Pan-NK Cells | FITC | DX5 | BioLegend |

FIG. 23B

| | | | | | |
|---|---|---|---|---|---|
| Flow cytometry | 3, 4, S1, S6, S7, S12 | Rat anti-mouse CD11b | PerCP-Cy5.5 | M1/70 | BioLegend |
| Flow cytometry | S12 | Rat anti-mouse IL-12/IL-23 P40 | PE | C15-6 | BioLegend |
| Flow cytometry | 4, S1, S7, S13 | Hamster anti-mouse FcεRIα | PE | MAR-1 | eBioscience |
| Flow cytometry | S12 | Rat anti-mouse interleukin-4 (IL-4) | FITC | BVD6-24G2 | eBioscience |
| Flow cytometry | 3, S12 | Hamster anti-mouse FcεRIα | Alexa Fluor®-647 | MAR-1 | eBioscience |
| Flow cytometry | 4 | Rat anti-mouse BAFF/BLyS/TNSF13B | PE | 121808 | R&D Systems |
| Flow cytometry | 2 | Rat anti-mouse CD19 | PE-Cy5 | 6D5 | BioLegend |
| Flow cytometry | 2 | Rat anti-mouse CD138 | PE | 281-2 | BD Biosciences |
| Flow cytometry | 4, S13 | Rat anti-mouse I-A/I-E | Alexa Fluor®-647 | M5/114.15.2 | BioLegend |
| Flow cytometry | S1 | Rat anti-mouse CD4 | PerCP-Cy5.5 | RM4-5 | BD Biosciences |
| Flow cytometry (isotype control) | 3, S12 | Armenian Hamster IgG | Alexa Fluor®-647 | eBio299Arm | eBioscience |
| Flow cytometry (isotype control) | 4, S1, S7, S13 | Armenian Hamster IgG | PE | eBio299Arm | eBioscience |
| Flow cytometry (isotype control) | 3, 4, S1, S6, S7, S12 | Rat IgG2b, κ | PerCP-Cy5.5 | A95-1 | BD Biosciences |
| Flow cytometry (isotype control) | 4, S1, S7 | Rat IgG2b, κ | APC | A95-1 | BD Biosciences |
| Flow cytometry (isotype control) | 4, S13 | Rat IgG2a, κ | Alexa Fluor®-647 | RTK2758 | BioLegend |
| Flow cytometry (isotype control) | S1 | Rat IgG2a, κ | PerCP-Cy5.5 | R35-95 | BD Biosciences |
| Flow cytometry (isotype control) | 2 | Rat IgG2a, κ | PE-Cy5 | RTK4530 | BioLegend |
| Flow cytometry (isotype control) | S13 | Rat IgG2b, κ | PE-Cy5 | RTK4530 | BioLegend |
| Flow cytometry (isotype control) | 2, 4, S1, S12 | Rat IgG2a, κ | PE | RTK2758 | BioLegend |
| Flow cytometry (isotype control) | S12 | Rat IgG1, κ | FITC | R3-34 | BD Biosciences |
| Flow cytometry (isotype control) | 3 | Rat IgG1, κ | PE | R3-34 | BD Biosciences |
| Flow cytometry (isotype control) | 4, S1, S2, S3, S4 | Rat IgG2a, κ | APC | RTK2758 | BioLegend |
| Flow cytometry (isotype control) | 3, 4, S1, S7, S12, S13 | Rat IgM, κ | FITC | RTK2118 | BioLegend |
| Flow cytometry (isotype control) | 6, S15 | Mouse IgG1, κ | PE | MOPC-21 | BioLegend |
| Flow cytometry (isotype control) | 6, S15 | Mouse IgG2b, κ | FITC | MPC-11 | BioLegend |
| Flow cytometry (isotype control) | 6, S15 | Mouse IgG1, κ | APC | MOPC-21 | BioLegend |

FIG. 23C

| | | | | | |
|---|---|---|---|---|---|
| Flow cytometry (isotype control) | 6, S15 | Mouse IgG2a, κ | PerCP-Cy5.5 | MOPC-173 | BioLegend |
| Flow cytometry (isotype control) | 6, S15 | Mouse IgG1, κ | PerCP-Cy5.5 | MOPC-21 | BioLegend |
| Flow cytometry (isotype control) | 6, S15 | Mouse IgG2b, κ | APC | MG2b-57 | BioLegend |
| Flow cytometry (Immunofluorescence) | S9 | Rat IgG2a, κ | FITC | RTK2758 | BioLegend |
| Flow cytometry (Immunofluorescence) | S2, S3, S4, S9 | Goat Anti-Mouse IgM (Human Adsorbed) | FITC | Polyclonal | Serotec Inc |
| Flow cytometry (Immunofluorescence) | S2, S3, S4, S9 | Goat Control Antibody | FITC | Polyclonal | Serotec Inc |
| Immune complexes | 3, S12 | Rat anti-mouse IgE | - | R35-92 | BD Biosciences |
| Immune complexes | 3, S12 | Mouse IgG1,K | - | MOPC21 | Sigma-Aldrich |
| Immune complexes | 3, S12 | Goat anti-mouse IgG | - | Polyclonal | Sigma-Aldrich |
| Immunofluorescence | S9 | Rat anti-mouse Complement Component C3 | FITC | RmC11H9 | Cedarlane Lab. |
| Immunofluorescence | 1, S9 | Goat Anti-Mouse IgG, Fc fragment F(ab')2 | FITC | Polyclonal | Sigma-Aldrich |
| Immunofluorescence, western blot | S10 | Rat anti-mouse IgE | FITC | R35-72 | BD Biosciences |
| Immunofluorescence, western blot | S9, S10 | Goat anti-mouse IgA | FITC | Polyclonal | Serotec Inc |
| Western blot | 3, S10 | Goat anti-rat IgG | Alexa Fluor®-680 | Polyclonal | Invitrogen |
| Western blot | 3, S10 | Goat anti-rat IgG | IR-Dye® 800 | Polyclonal | Rockland IC |
| Western blot | S10 | Donkey anti-rat IgG | Alexa Fluor®-680 | Polyclonal | Invitrogen |

HRP: Horseradish Peroxydase
FITC: Fluorescein
PE: Phycoerithrin
PerCP-Cy5.5: Peridinin-chlorophyll-protein complex - Cyanin 5.5
PE-Cy5: Phycoerithrin - Cyanin 5
APC: Allophycocyanin

COMPOSITIONS AND METHODS FOR TREATING OR PREVENTING LUPUS

CROSS-REFERENCE TO RELATED APPLICATIONS

This application is a continuation application of U.S. patent application Ser. No. 13/989,744, filed 15 Jan. 2014, entitled COMPOSITIONS AND METHODS FOR TREATING OR PREVENTING LUPUS, which is a 35 U.S.C. § 371 U.S. national entry of International Application PCT/US2010/058077 (International Application Publication WO 2012/071042), filed 24 Nov. 2010, both of which are incorporated herein by reference in their entireties for all purposes.

STATEMENT OF RIGHTS TO INVENTIONS MADE UNDER FEDERALLY SPONSORED RESEARCH

Research supporting this application was carried out by the United States of America as represented by the Secretary, Department of Health and Human Services. The Government has certain rights in this invention.

BACKGROUND OF THE INVENTION

Systemic lupus erythematosus (SLE) is a complex disease affecting various organs and may result in death when kidney damage (lupus nephritis) is severe. Lupus nephritis is characterized by IgM-, IgG-, and IgA-containing immune complexes deposited in the glomeruli. These immune complexes are formed by autoantibodies with specificity to nuclear components (antinuclear antibodies (ANA)) or to nucleic acids (such as double-stranded DNA (dsDNA)). Current methods for treating lupus or the resulting nephritis are inadequate, and improved methods of treating or preventing lupus and/or lupus nephritis are needed.

SUMMARY OF THE INVENTION

As described below, the present invention features compositions and methods useful for treating and/or preventing lupus, lupus nephritis, lupus-related, and other autoimmune disorders The invention provides composition and methods for treating and/or preventing lupus, lupus nephritis, lupus-related disorders, and other autoimmune disorders by reducing the production or biological activity of autoreactive IgE, IgE receptor, reducing basophil activation, and/or depleting basophils. Compositions and articles defined by the invention were isolated or otherwise manufactured in connection with the examples provided below.

In one aspect, the invention generally features a method for treating or preventing lupus, lupus nephritis, lupus-related, and/or other autoimmune disorders in a subject in need thereof, the method involving administering to the subject an effective amount of an agent that reduces the expression or biological activity of IgE or an IgE receptor in the subject.

In another aspect, the invention generally features a method of treating or preventing lupus, lupus nephritis, lupus related, and/or other autoimmune disorders in a subject in need thereof, the method involving administering to the subject an effective amount of an agent that decreases the number or activity of basophils or that reduces basophil activation in the subject.

In yet another aspect, the invention features a method of treating or preventing lupus, lupus nephritis, lupus-related, and/or other autoimmune disorders in a subject involving administering to a subject in need thereof an effective amount of omalizumab.

In further aspects, the invention features a pharmaceutical composition for the treatment or prevention of lupus nephritis containing a therapeutically effective amount of an anti-IgE therapy (e.g. omalizumab or other administered agent) combined with a further, distinct agent selected from the group consisting of nonsteroidal anti-inflammatory drugs (NSAIDs), hydroxychloroquine, corticosteroids, cyclophosphamide, azthioprine, methotrexate, mycophenolate, belimumab, dehydroepiandrosterone, and rituximab.

In additional aspects, the invention features a pharmaceutical composition for the treatment or prevention of lupus nephritis containing a therapeutically effective amount of an agent that inhibits basophils or decreases the numbers of basophils.

In yet another aspect, the invention features a kit for the treatment or prevention of lupus, lupus nephritis, and lupus-related disorders, the kit comprising an effective amount of an agent that reduces the expression or biological activity of IgE and directions for using the kit for the treatment of lupus, lupus nephritis, and lupus-related disorders according to any of the methods described herein. A preferred therapeutic agent of the pharmaceutical compositions and kits of the invention is omalizumab.

In various embodiments of any of the above aspects or any other aspect of the invention delineated herein, the agent is a polypeptide, nucleic acid molecule or small compound. In another embodiment the polypeptide is an antibody or fragment thereof that selectively binds IgE, an IgE receptor, or regulates production of IgE. In further embodiments the antibody fragment is an Fab or single chain V region fragment (scFv). In yet another embodiment the nucleic acid molecule is an siRNA, antisense polynucleotide, or shRNA that reduces IgE expression. In additional embodiments the small molecule compound is a Syk kinase inhibitor. In other embodiments the Syk kinase inhibitor is fostamatinib. In further embodiments the small molecule compound regulates IgE production or basophil activation. In yet other embodiments the agent modulates a microRNA that antagonizes IgE production. In another embodiment the method reduces the level of autoreactive IgEs and/or reduces the level of circulating immune complexes. In additional embodiments the method reduces basophil activation. In further embodiments the method reduces levels of one or more of CD203c expression, CD62L, and HLA-DR in said subject.

In other preferred embodiments, the administered agent is omalizumab. In certain aspects, the effective administered amount of omalizumab is between about 75 mg to 500 mg per dose. In another embodiment omalizumab is administered every 1, 2, 3, or 4 or more weeks at about 150 mg-400 mg per dose.

In further embodiments the subject is identified as having or having a propensity to develop lupus or lupus nephritis, and the therapeutic agent is administered to such identified subject. In yet another embodiment the subject has elevated IgE levels. In further embodiments the agent is a monoclonal anti-IgE antibody. In yet further embodiments of the invention the monoclonal anti-IgE is a humanized monoclonal antibody. In additional embodiments the monoclonal anti-IgE antibody is omalizumab. In yet additional embodiments the method further comprises administering to the subject an agent selected from the group consisting of nonsteroidal anti-inflammatory drugs (NSAIDs), hydroxychloroquine, corticosteroids, cyclophosphamide, azthioprine, methotrexate, mycophenolate, belimumab, dehydroepiandrosterone, and rituximab. In other embodiments the lupus nephritis is diffuse proliferative lupus nephritis or membranous lupus nephritis. In another embodiment the autoimmune disorder is selected from the group consisting of Sjögrens syndrome, rheumatoid arthritis, antiphospholipid syndrome, myositis, and scleroderma. In further embodiments the anti-IgE therapy comprises a monoclonal anti-IgE antibody. In yet further embodiments the anti-IgE therapeutic comprises an antibody. In another embodiment the anti-IgE therapeutic comprises a monoclonal antibody. In other embodiments the anti-IgE therapeutic is omalizumab.

Definitions

By "omalizumab" is meant a recombinant DNA-derived humanized IgG monoclonal antibody that selectively binds to human immunoglobulin E (IgE). Omalizumab as referred to herein also designates the antibody clinical agent identified under the tradename Xolair.

The term "anti-IgE therapy" is used in its customary meaning herein and includes a treatment regimen that inhibits or blocks the expression and/or function of IgE or that clears or reduces the half-life of IgE in a subject such as a primate including a human.

By "autoreactive or self-reactive IgE" is meant an IgE immunoglobulin that is directed to an epitope present in the host. Methods for measuring IgE or autoreactive IgE include ELISA. Luminex, or other platforms that allow measurement of autoreactive IgE to known antigens, such as dsDNA, ANA, La, Ro, Sm, phospholipids, etc.

By "basophil activation" is meant the process whereby IgE binding to the Fc Receptor for IgE ("FcεR") leads to the degranulation of basophils. Methods for measuring basophil activation, number, or activity include, but are not limited to, measuring CD203c expression on the surface of basophils.

The terms "lupus" or "systemic lupus erythematosus (SLE)" are used in their customary meaning herein and include an autoimmune disorder characterized by the presence of autoantibodies, rash, oral ulcers, serositis, neurological disorders, low blood cell counts, joint pain and swelling. Tests used to diagnose include antibody tests (e.g., Antinuclear antibody (ANA) panel, Anti-double strand (ds) DNA, Antiphospholipid antibodies, Anti-Smith antibodies); CBC to show low white blood cells, hemoglobin, or platelets; chest x-ray showing pleuritis or pericarditis; kidney biopsy; urinalysis to show blood, casts, or protein in the urine.

By "lupus nephritis" is meant a disorder characterized by an inflammation of the kidney caused by systemic lupus erythematosus (SLE).

By "lupus-related disorder" is meant any pathological condition characterized by self-reactive IgE and basophil activation. Such disorders include, but are not limited to Sjögrens syndrome, rheumatoid arthritis antiphospholipid syndrome, myositis, scleroderma, and others.

By "fostamatinib" is meant an orally available Syk kinase inhibitor that blocks IgG Fc receptor signaling. Fostamatinib has the following chemical structure:

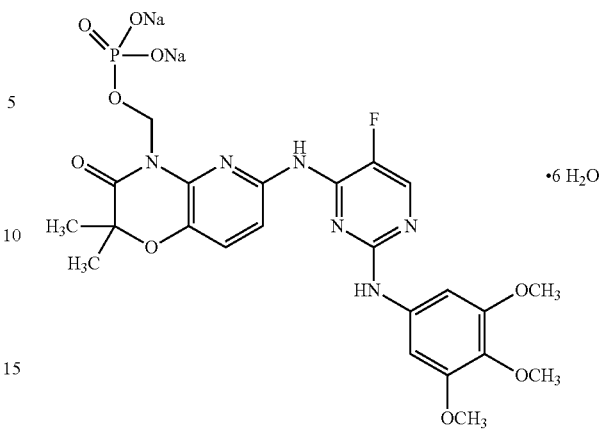

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include lupus, systemic lupus erythematosus, lupus nephritis, Sjögrens syndrome, rheumatoid arthritis antiphospholipid syndrome, myositis, scleroderma, and others.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µm/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a graph of flow cytometric analysis of non-depleted (Baso +) or basophil-depleted (Baso −) peripheral blood cells from aged (30 weeks) WT and $Lyn^{-/-}$ mice. Data shown are representative of at least 3 animals per group.

Data was collected on CD11b$^+$ leukocytes. In FIGS. 1B-1D splenocytes from WT and Lyn$^{-/-}$ mice were harvested, incubated with 10 μM monensin, labeled with a fluorescent anti-CD4 antibody, and stained for intracellular IL-4 and IFN-γ. FIG. 1B is a representative flow cytometric analysis of CD4$^+$ cells from WT or Lyn$^{-/-}$ mice, non-depleted (Baso +) or basophil-depleted (Baso −) (as shown in FIG. 1A). FIG. 1c is a graph of the compilation of all individual experiments as in FIG. 1B for CD4$^+$IL-4$^+$ T cells. FIG. 1D is a graph of the compilation of all individual experiments as in FIG. 1B for CD4$^+$ IFN-γ$^+$ T cells. Statistical analysis was by a two tailed unpaired student t test; *: p<0.05; **: p<0.01; NS: not significant.

FIGS. 2A, 2B, and 2C show that the proportion of blood B cells in Lyn$^{-/-}$ mice is independent of IgE, IL-4 and mast cells. In FIGS. 2A-2C, B cell (B220$^+$IgM$^+$) proportion of the leukocytes was determined by flow cytometry in four distinct age groups in the indicated genotypes. Age group 1: 5 to 10 weeks old (average=7.5 weeks); age group 2: 12 to 14 weeks old (average=13 weeks); age group 3: 17 to 20 weeks old (average=18.5 weeks); age group 4: 35-40 weeks old (average=37.5 weeks). FIG. 2A is a graph showing that for Igh7$^{+/+}$ Lyn$^{+/+}$ and Igh7$^{-/-}$ Lyn$^{-/-}$, per group and per genotype, n=12; For WT, n=10 and Lyn$^{-/-}$ n=12. WT and Lyn$^{-/-}$ mice were on a C57BL/6 background. FIG. 2B is a graph showing that for Il-4$^{+/+}$ Lyn$^{+/+}$ and Il-4$^{-/-}$ Lyn$^{-/-}$, per group and per genotype, n=12; For WT, n=10 and Lyn$^{-/-}$ n=12. FIG. 2C is a graph showing that for Kit$^{W-sh/W-sh}$ and Kit$^{W-sh/W-sh}$ Lyn$^{-/-}$, group 1: n=9 per genotype, group 2: n=3 per genotype, group 3: n=11 per genotype, group 4: n=10 per genotype; For WT n=10 and Lyn$^{-/-}$ n=12. Data are shown as means±s.e.m. Statistical analysis was realized by using a two way ANOVA test of variances. The p value shown is the genotype factor p value.

FIGS. 3A, 3B, and 3C show that the proportion of spleen B cells in Lyn deficient mice is independent of IgE, IL-4, and mast cells. In FIGS. 3A-3C, B cell (B220$^+$IgM$^+$) proportion of the splenocytes was determined by flow cytometry in four distinct age groups in the indicated genotypes as described in FIGS. 2A-2C. Data are shown as means±s.e.m. Statistical analysis was realized by using a two way ANOVA test of variances. The p value shown is the genotype factor p value.

FIGS. 4A, 4B, 4C, 4D, 4E, and 4F show that bone marrow B cell proportion phenotype of Lyn deficient mice is independent of IgE, IL-4, and mast cells. In FIGS. 4A, 4C, and 4E total B cell (B220$^+$IgM$^+$) proportion of the bone marrow cells was determined by flow cytometry in four distinct age groups in the indicated genotypes as described in FIG. 2. In FIGS. 4B, 4D, and 4F, recirculating B1 cells (B220$^{hi}$IgM$^{int}$) proportion of the BM cells was determined in the same groups. Data are shown as means±s.e.m. Statistical analysis was realized by using a two way ANOVA test of variances. The p value shown is the genotype factor p value.

FIGS. 5A, 5B, 5C, 5D, 5E, and 5F show serum levels of the different immunoglobulin isotypes in the studied mice. Serum quantification by ELISA of circulating IgM (FIG. 5A), IgE (FIG. 5B), IgA (FIG. 5C), IgG1 (FIG. 5D), IgG2a (FIG. 5E) and IgG2b (FIG. 5F) in all the genotypes used in this study. WT, n=35; Lyn$^{-/-}$ n=35; Igh7$^{+/+}$ Lyn$^{+/+}$ n=43; Igh7$^{-/-}$ Lyn$^{-/-}$ n=41; Igh7$^{-/-}$, n=3; Il-4$^{+/+}$ Lyn$^{+/+}$, n=41; Il-4$^{-/-}$ Lyn$^{-/-}$, n=42; Il-4$^{-/-}$, n=4; Kit$^{W-sh/W-sh}$, n=18 and Kit$^{W-sh/W-sh}$Lyn$^{-/-}$, n=18. Data shown are means±s.e.m. Statistical analysis was by a two tailed unpaired student t test; *: p<0.05; : p<0.01; *: p<0.001.

FIGS. 6A, 6B, 6C, 6D, 6E, and 6F show splenomegaly and spleen proportion of CD11b$^+$ cells of Lyn deficient mice are independent of IgE, IL-4 and mast cells. In FIGS. 6A, 6C, and 6E, total spleen weight was determined for the spleen from four distinct age groups in the indicated genotypes as described in FIG. 2. In FIGS. 6B, 6D, and 6F the proportion of CD11b$^+$ cells in the spleen from the same groups was determined by flow cytometry. Data are shown as means±s.e.m. Statistical analysis was realized by using a two way ANOVA test of variances. The p value shown is the genotype factor p value.

FIGS. 7A, 7B, 7C, 7D, 7E, 7F, and 7G show that mast cell but not basophil phenotypes of Lyn deficient mice are dependent on IgE, but both are IL-4 independent. In FIGS. 7A, 7C, and 7E the proportion of mast cells (FcεRIα$^+$ CD117$^+$) in the peritoneum was determined by flow cytometry after peritoneal lavage in four distinct age groups for the indicated genotypes as described in FIG. 2. In FIGS. 7B, 7D, 7F, and 7G, the proportion of basophils (FcεRIα$^+$CD49b$^+$ CD11b$^+$ CD117$^-$) in the total leukocyte population was determined by flow cytometry in the same groups. (FIGS. 7A and 7B) For Igh7$^{+/+}$ Lyn$^{+/+}$ and Igh7$^{-/-}$ Lyn$^{-/-}$, per group and per genotype, n=12; For WT, n=10 and Lyn$^{-/-}$, n=12. (FIGS. 7C and 7D) For Il-4$^{+/+}$Lyn$^{+/+}$ and Il-4$^{-/-}$Lyn$^{-/-}$, per group and per genotype, n=12; For WT, n=10 and Lyn$^{-/-}$ n=12. (FIGS. 7E and 7F) group 1: WT n=8 and Lyn$^{-/-}$ n=11, group 2: WT n=14 and Lyn$^{-/-}$ n=9, group 3: WT n=14 and Lyn$^{-/-}$ n=11, group 4: WT n=10 and Lyn$^{-/-}$ n=12. (FIG. 7G) For Kit$^{W-sh/W-sh}$ and Kit$^{W-sh/W-sh}$ Lyn$^{-/-}$, group 1: n=9 per genotype, group 2: n=3 per genotype, group 3: n=11 per genotype, group 4: n=10 per genotype; For WT n=10 and Lyn$^{-/-}$ n=12. Data are shown as means±s.e.m. Statistical analysis was realized by using a two way ANOVA test of variances. The p value shown is the genotype factor p value.

FIG. 8A shows the glomerulonephritis scores obtained from H&E-stained histological kidney sections from aged mice (over 40 weeks) of the indicated genotypes. Data shown as means±s.e.m. (for WT and Lyn$^{-/-}$: n=8; for WT and Igh7$^{-/-}$; Lyn$^{-/-}$: n=6; for WT and Il-4$^{-/-}$; Lyn$^{-/-}$: n=5; for Kit$^{W-sh/W-sh}$ and Kit$^{W-sh-W-sh}$; Lyn$^{-/-}$: n=11). Statistical analysis was by a two-tailed unpaired Student's t test; *P<0.001; NS, not significant. FIG. 8B is a panel of photomicrographs of representative glomeruli in H&E-stained histological kidney sections of aged mice (40-weeks-old) of the indicated genotypes. Scale bar, 50 μm. FIG. 8C is a panel of photomicrographs of immunofluorescent detection of glomerular IgG deposits in aged mice (40 weeks) of the indicated genotypes after staining with fluorescein-conjugated antibody to mouse IgG. Scale bar, 50 μm. FIG. 8D is a graph of ACR measured in the urein of a minimum of 15 aged mice (40 weeks) of the indicated genotype per group. Data are means±s.e.m. Statistical analysis was by a two-tailed unpaired Student's t test; *P<0.001.

In FIGS. 10A-10C, kidneys from 40 weeks old mice of the indicated genotypes were processed as described in methods. Immunofluorescent staining with fluorescein-conjugated antibodies raised against the indicated antigens was realized (FIG.

10A, IgM; FIG. 10B, IgA; FIG. 10C, complement component 3 (C3)). Pictures shown are representative of over 100 glomeruli per genotype acquired on at least 5 different 40 weeks old mice per genotype. Original magnification ×40. Scale bar, 50 μm.

FIG. 11A is a graph of the quantification of dsDNA-specific IgG in the serum of aged mice (40 weeks) of the indicated genotype. Data are means±s.e.m. (at least 15 mice per group). FIG. 11B is a graph of the quantification of ANA-specific IgG in the mice studied in FIG. 11A. FIG. 11C is a graph of quantification of ANA-specific IgG autoantibodies in the serum of aged mice (32 weeks) of the indicated genotypes before (DO) and six days after (D6) injection of the basophil-depleting antibody MAR-1(−) or isotype control (+). Data are means±s.e.m. (WT: n=3; $Lyn^{-/-}$ (+): n=4; $Lyn^{-/-}$ (−): n=5). FIG. 11D is a graph of the same quantification as in FIG. 11C for the serum of mice (20-weeks-old) of the indicated genotypes. Data are means±s.e.m. (for each group, n=3). FIG. 11E plots the proportion of splenic $CD138^+CD19^+$ plasma cells determined by flow cytometry in mice 6 days after basophil depletion (−) or isotype injection (+). Cytokine amounts were normalized to the total protein content unpaired (FIGS. 11A, 11B, 11E, and 11F) or paired (FIGS. 11C and 11D) Student's t test; *P<0.05; P<0.01; *P<0.001.

FIGS. 12A-12D are graphs of the ELISA quantitation of the indicated cytokines in kidney homogenates from 40 week old WT and $Lyn^{-/-}$ mice 6 days after basophil depletion (MAR-1 injection, basophils −) or not (isotype injection, basophils +) as described in methods. Cytokine amounts were normalized to the total protein content of the respective homogenates. Data are shown as mean±s.e.m. (WT and $Lyn^{-/-}$, at least n=4 per group). Statistical analysis was by a two tailed unpaired student t test; NS: not significant, *: p<0.05.

FIG. 13A is a plot of quantification of dsDNA-specific IgE in the sera of aged mice (40 weeks) of the indicated genotypes, as determined by semiquantitative ELISA. Data are shown as mean±s.e.m. (more than ten mice per group) normalized to the respective WT control and expressed as arbitrary units. Statistical analysis was by a two-tailed unpaired Stundent's t test; *P<0.05; ***P<0.001. In FIG. 13B, IgE-CICs and IgG-CICs from serum samples of $Igh7^{-/-}$; $Lyn^{-/-}$ and $Il-4^{-/-}$; $Lyn^{-/-}$ aged mice (>30-weeks-old) are reduced. Western blots were probed with antibody to mouse IgE or antibody to mouse IgG. One representative of at least ten mice per genotype is shown. FIG. 13C is a graph of serum levels of CICs (IgA, IgM, and IgG), as determined by semiquantitative ELISA from at least ten aged mice per genotype on complent factor 1q (C1q)-coated plates. Data are shown as mean±s.e.m. normalized to levels in WT mice and reported as arbitrary units. Statistical analysis was by a two-tailed unpaired Student's t test; *P<0.05; P<0.01; *P<0.001. FIG. 13D is a plot of IL-4 production from (bone marrow-derived) basophils induced by the indicated stimuli. PMA+ionomycin, phorbol 12-myristate 13-acetate (20 nM) plus ionomycin (400 nM). The mean fluorescence intensity (MFI) detected by intracellular staining of IL-4 was normalized to the response of the unstimulated (−) control and expressed as arbitrary units. Data are shown as mean±s.e.m. (n=6 per condition for three independent experiments). Statistical analysis was by a two-tailed paired Student's t test; *P<0.05; **P<0.01.

FIG. 14A is a western blot analysis of $PEG_{6000}$ precipitated circulating immune complexes (CIC) from sera from 5 different 45 weeks old WT and $Lyn^{-/-}$ mice (1 to 5 for each genotype). FIG. 14A Upper panel: Rat anti-mouse IgE immunoblot (IgE-CIC). FIG. 14 A Middle panel: ELISA quantification of total serum IgE in the same mice showing no correlation between the level of total IgE and the amount of IgE-CIC precipitated (upper panel). FIG. 14 A Lower panel: densitometry analysis of immunoblots similar to the one shown in the upper panel using the NIH Image J software. FIG. 14B same as in FIG. 14A for IgG-CIC with goat anti-mouse IgG (upper panel), total IgG ELISA (middle panel) and densitometry analysis of IgG-CIC (lower panel). FIG. 14C same as in FIG. 14A for IgA-CIC with goat anti-mouse IgA (upper panel), total IgA ELISA (middle panel) and densitometry analysis of IgA-CIC (lower panel). FIGS. 14D and 14E are plots of the quantified immunoblots as the representative ones shown in FIGS. 14A and 14B were quantified by densitometry as in FIGS. 14A-14C for IgE-CIC FIG. 14D and IgG-CIC FIG. 14E. All genotypes were analyzed. Data are shown as means±s.e.m. (WT and $Lyn^{-/-}$, n=10 per group, all other genotypes, n=5 per group). Data presented are representative of at least five independent experiments.

FIGS. 15A and 15B are representative flow cytometry analysis of IL-4 production by bone-marrow derived basophils (BMBa) in WT and $Lyn^{-/-}$ mice. Cells were stimulated for 4 hours with the indicated stimulus and incubated with 10 μM monensin during the last two hours of stimulation. Cells were then extracellularely stained for mouse basophils markers (CD49b, FcεRIα and CD11b) and intracellularely stained for IL-4 production. Compilation of all these results is shown in FIG. 13D. FIG. 15C uses the same protocol as in FIGS. 15A and 15B but cells were intracellularely stained for IL-12p40 production. Filled: isotype control, dashed: IgE+Ag stimulated BMBa, solid black: PMA/ionomycin stimulated BMBa, solid grey: BM cell population $CD49b^-$ $FcεRIα^-$ (non-basophil, non-mast cell) producing IL-12p40 after PMA/ionomycin stimulation. FIG. 15D is the same as in FIG. 15C but cells were intracellularely stained for IFN-γ production. In FIGS. 15C and 15D none of the stimuli tested (as in FIGS. 15A and 15B) led basophils to produce either IL-12p40 or IFN-γ.

FIGS. 16A, 16B, 16C, 16D, 16E, 16F, and 16G shows that basophils from aged $Lyn^{-/-}$ mice upregulate CD62L expression, home to secondary lymphoid tissues and express membrane BAFF and MHC II. FIG. 16A is a representative flow cytometric analysis of blood basophil CD62L expression in aged (40 weeks) WT (gray dashed line) and $Lyn^{-/-}$ mice (black line) relative to isotype control (gray fill). FIG. 16B is pooled data from all experiments performed as in FIG. 16A from aged mice of the indicated genotype. The mean fluorescence intensity (MFI) of CD62L expression on blood basophils was normalized to corresponding WT controls and expressed as means±s.e.m. in arbitrary units (WT and $Lyn^{-/-}$: n=4 and n=7; WT and $Igh7^{-/-}$; $Lyn^{-/-}$: n=3; WT and $Il-4^{-/-}$; $Lyn^{-/-}$: n=3; $Kit^{W-sh/W-sh}$ and $Kit^{W-sh/W-sh}$; $Lyn^{-/-}$: n=4 and n=7). Statistical analysis was by a two-tailed unpaired Student's t test; *P<0.05. FIGS. 16C-16E are flow cytometric analysis of basophils (defined as FcεRI+ CD11b+ CD49b+ cells) in lymph nodes (cervical and inguinal) FIG. 16C, spleen FIG. 16D, and blood 16E of the indicated mouse strains relative to the total cell number. FIGS. 16F and 16G are representative flow cytometric analysis of basophil membrane BAFF (FIG. 16F) or MHC II (I-A/I-E) (FIG. 16G) expression in the lymph nodes of Lyn$^{-/-}$ mice (black line) relative to isotype control (gray fill).

FIG. 17 shows that MHC II expression is increased on spleen basophils from Lyn$^{-/-}$ mice. Representative flow cytometric analysis of spleen basophil MHC II expression (I-A/I-E). Basophils were defined as FcεRI+ CD117− CD49b+ cells, in aged (40 weeks) WT (left panel, black line) and Lyn$^{-/-}$ mice (right panel, black line) relative to isotype control (grey fill).

FIG. 18A shows total CICs in serum from healthy controls (n=37), individuals with inactive SLE (SLEDAI=0) (n=13), individuals with mild disease (SLEDAI=2.0 to ≤4.0) (n=15) and individuals with active disease (SLEDAI>4) (n+15), as measured by ELISA. Data are means±s.e.m. Statistical analysis was by a two-tailed unpaired Student's t test; *P<0.05; P<0.01; *P<0.001. FIG. 18B graphs the dsDNA-specific IgE levels, as determined by semiquantitative ELISA. dsDNA-coated plates were incubated with sera from healthy controls and subjects with SLE (the same populations as in FIG. 18A). Data are means±s.e.m. (same n as in FIG. 18A) normalized to healthy controls. Statistical analysis was by a two-tailed unpaired Student's t test; *P<0.05; *P<0.001. FIG. 18C plots IgE-specific IgG levels, as determined by incubating sera from healthy controls and individuals with SLE on human IgE-coated plates. IgE-specific IgG was detected with antibody to human IgG (Fcγ specific). Data are means±s.e.m. (same n as in FIG. 18A) normalized to healthy controls. Statistical analysis was by a two-tailed unpaired Student's t test; P<0.01. FIG. 18D is dsDNA-specific IgE in sera of subjects with SLE classified on the basis of active nephritis (yes, n=8) or not (no, n=34). Data are means±s.e.m. Statistical analysis was by a two-tailed unpaired Student's t test.

FIG. 19A is a plot of the quantitation of total serum IgE levels in healthy controls (n=27) and SLE patients (n=33) by ELISA. FIG. 19B is the same measurement as in FIG. 19A but showing its relationship to inactive/moderate/active SLE patients ((n=9/13/11) as described in FIG. 18A) versus healthy controls (n=27). Data shown are means±s.e.m. Statistical analysis was by a two tailed unpaired student t test; NS: not significant, *: p<0.05. (c) IgG anti-dsDNA subclasses and IgE anti-dsDNA was determined by semi-quantitative ELISA. dsDNAcoated plates were incubated with sera from healthy controls (n=5) and SLE patients (n=43) and autoreactive IgG1, IgG2, IgG3, IgG4 and IgE were detected with the corresponding specific anti-human Fc portion HRP-conjugated. Data shown are normalized to healthy controls and expressed as means±s.e.m.

FIG. 20A is a graph of flow cytometric analysis of the levels of activated blood basophils (CD203c expression) relative to disease intensity from subjects with inactive, mild, or active SLE ((n=13, n=15, and n=15, respectively) as defined in the legend for FIG. 18A compared to controls (n=41). Data are the ratio of CD203c mean fluorescence intensity (MFI) normalized to controls and expressed in arbitrary units. FIG. 20B is a plot of flow cytometric analysis of CD62L expression (MFI) on blood basophils in subject groups as in FIG. 20A. Data are normalized as in FIG. 20A and are expressed as means±s.e.m. in arbitrary units (AU) (healthy controls: n=13; SLE patients: inactive/mild/active n=4/6/6). FIG. 20D is a plot of the absolute number of blood basophils (healthy controls: n=41; inactive SLE: n=13; moderate SLE: n=15; active SLE: n=15) as determined by flow cytometry. Data are means±s.e.m. In FIGS. 20A-20D, statistical analysis was by a two-tailed unpaired Student's t test; *P<0.05; P<0.01; *P<0.001. FIGS. 20E and 20F are photomicrographs of immunohistochemistry (with the 2D7 monoclonal antibody) of basophils in the lymph nodes (FIG. 20E) or spleen (FIG. 20F) of healthy (normal) controls or subjects with SLE (n=2). Basophils were found in the B cell zone of lymph node germinal centers in individuals with SLE only (FIG. 20E). A spleen biopsy from healthy (normal) controls or from an individual with SLE shows the localization of basophils in the germinal centers of subjects with SLE but not normal controls (FIG. 20F). Similar results were obtained with a second basophil-specific antibody (BB1) (data not shown). Original magnification, ×20. Scale bar, 200 μm. Insets show the boxed area of the larger images. Original magnification, ×40. Scale bars, 25 μm.

FIGS. 21A, 21B, 21C, and 21D show the effect of immunosuppressive treatments on blood basophil numbers and HLA-DR expression. FIG. 21A shows that peripheral blood basophil counts were significantly lower in patients receiving immunosuppressive treatment (IST) (defined as prednisone more than 15 mg/day and/or cyclophosphamide, azathioprine, mycophenolate mofetil). FIGS. 21B and 21D shows that there was no difference on the number of peripheral basophils (FIG. 21B) or HLA-DR expressing basophils (FIG. 21D) among patients receiving low dose (≤7.5 mg/day) or medium to high dose (>7.5 mg/day) prednisone. FIG. 21C shows that there was no difference in proportion of HLA-DR+ basophils between patients on or off IST. Data shown are means±s.e.m. Statistical analysis was by a two tailed unpaired student t test.

FIG. 22 is a table showing the demographics and characteristics of SLE patients.

FIG. 23 is a table of the commercially available antibodies that were used.

DETAILED DESCRIPTION OF THE INVENTION

Figure 1A:
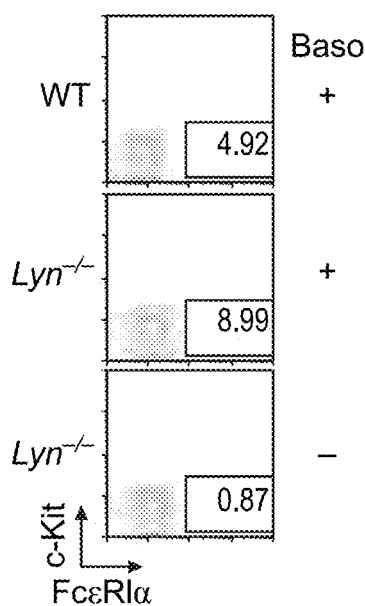
FIGS. 1A, 1B, 1C, and 1D show that basophil-dependent $T_H2$ skewing is a prominent feature of aged $Lyn^{-/-}$ mice.
Figure 1B:
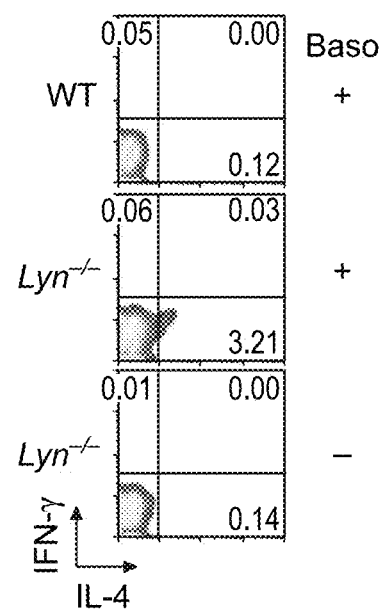
Figure 1C:
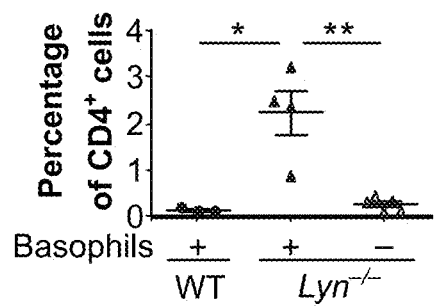
Figure 1D:
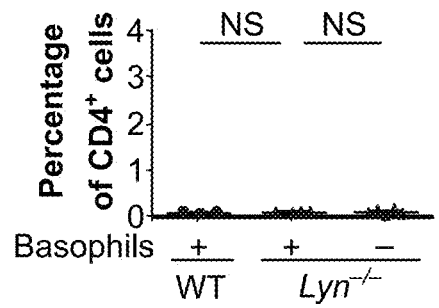
Figures 5A, 5B, 5C:
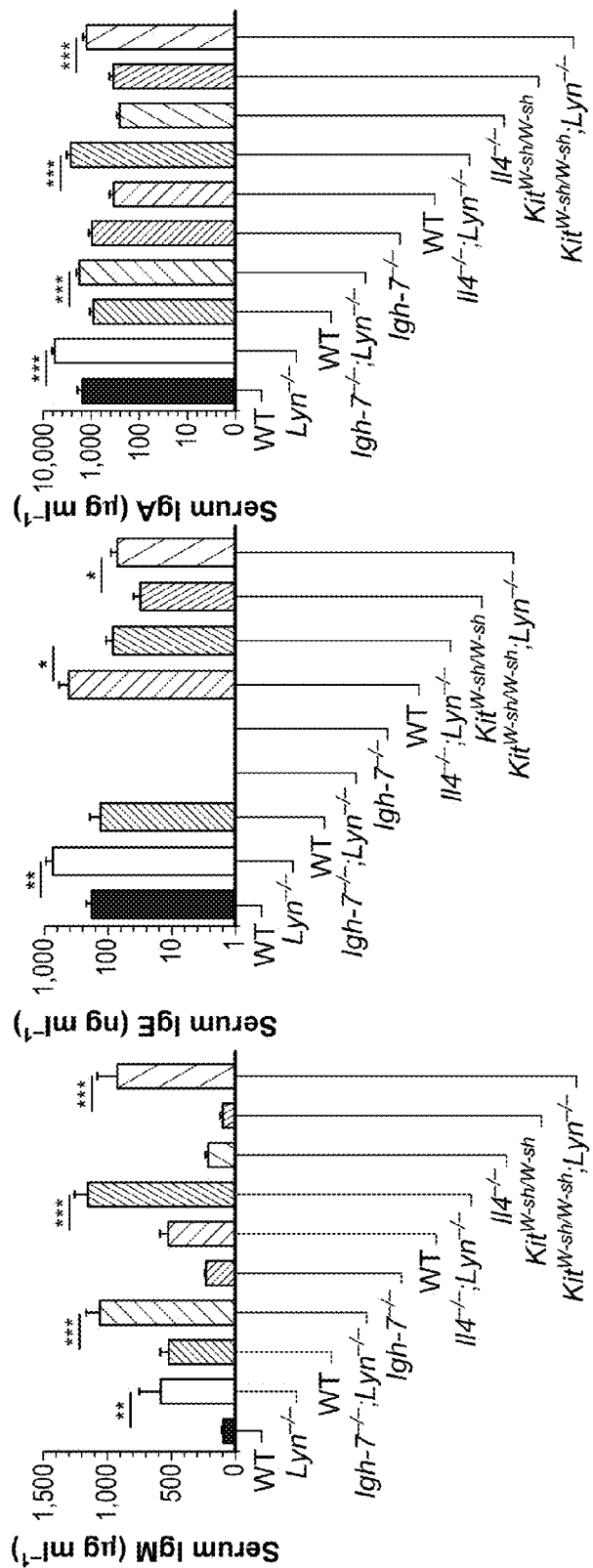
Figure 7A:
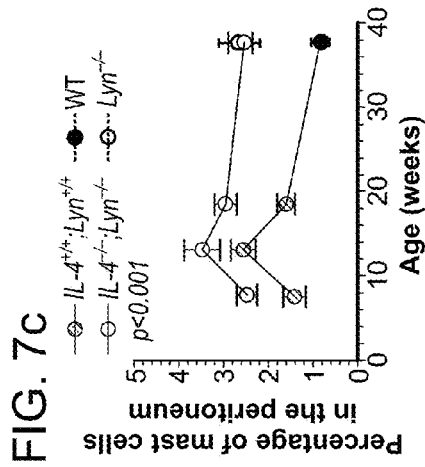
Figure 7B:
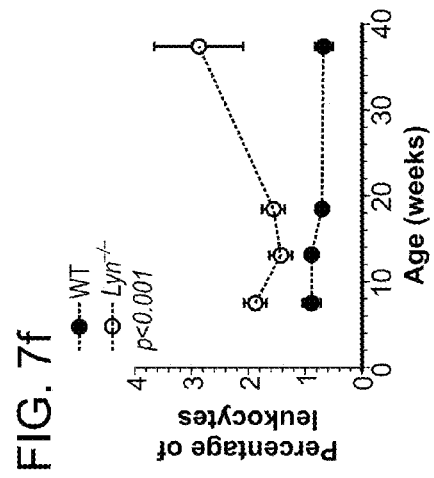
Figure 7C:
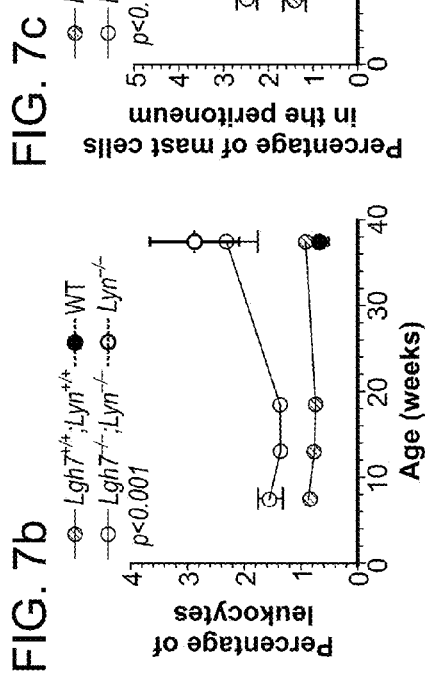
Figure 7D:
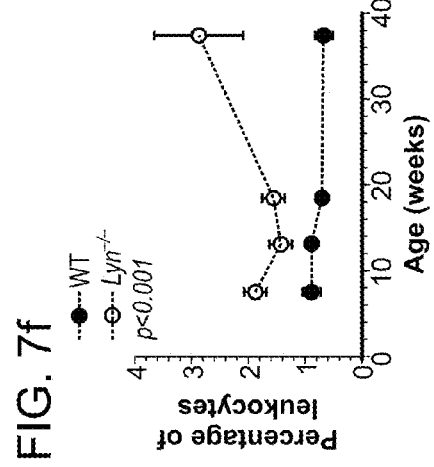
Figure 7E:
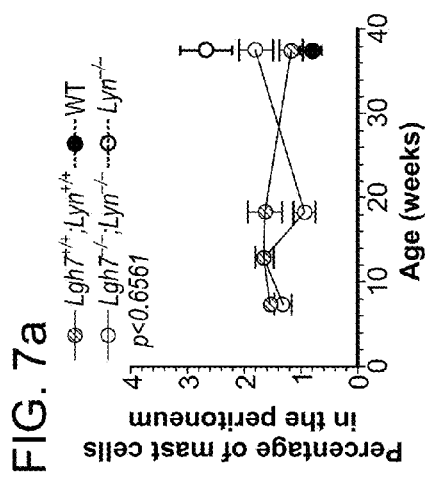
Figure 7F:
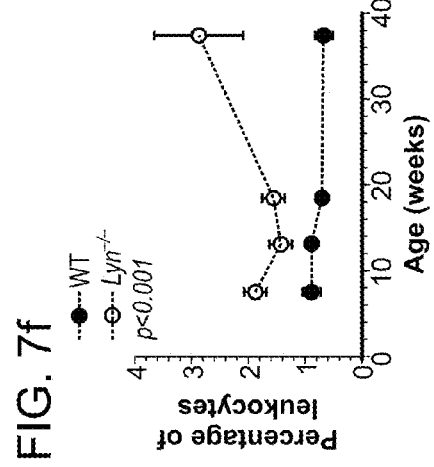

The invention features compositions and methods that are useful for the treatment of lupus, lupus nephritis, lupus-related disorders, and other autoimmune disorders.

The invention is based, at least in part, on the discovery that activation of basophils by autoreactive IgE caused their homing to lymph nodes, promoting T helper type 2 ($T_H2$) cell differentiation and enhancing the production of self-reactive antibodies that cause lupus-like nephritis in mice lacking the Src family protein tyrosine kinase Lyn (Lyn$^{-/-}$ mice). Individuals with SLE also had elevated serum IgE, self-reactive IgEs and activated basophils that expressed CD62 ligand (CD62L) and the major histocompatibility complex (MHC) class II molecule human leukocyte antigen-DR (HLA-DR), parameters that are associated with increased disease activity and active lupus nephritis. Basophils were also present in the lymph nodes and spleen of subjects with SLE. These results indicate that basophils and IgE autoantibodies amplify autoantibody production that leads to lupus nephritis. Accordingly, the invention provides compositions and methods useful for preventing or treating lupus, lupus nephritis, lupus-related disorders, and other autoimmune disorders by inhibiting autoreactive IgE production, reducing basophil activation by autoreactive antibodies, or otherwise inhibiting undesirable basophil activity.

Systemic Lupus Erythematosus (SLE)

SLE is a complex disease affecting various organs and may result in death when kidney damage (lupus nephritis) is severe. (Rahman, A. & Isenberg, D. A., (2008) *N. Engl. J. Med.* 358, 929-939; Moser, K. L. et al., (2009) *Genes Immun.* 10, 373-379). Lupus nephritis is characterized by IgM-, IgG- and IgA-containing immune complexes deposited in the glomeruli. These immune complexes are formed by autoantibodies with specificity to nuclear components (antinuclear antibodies (ANA)) or to nucleic acids (such as double-stranded DNA (dsDNA)). Although there is considerable evidence for the role of $T_H1$, $T_H17$ and regulatory T cells in SLE, (Masutani, K. et al. (2001) *Arthritis Rheum.* 44, 2097-2106; Balomenos, D. et al., (1998) *J. Clin. Invest.* 101, 364-371; Peng, S. L. et al., (2002) *Proc. Natl. Acad. Sci. USA* 99, 5545-5550; Zeng, D. et al., (2003) *J. Clin. Invest.* 112, 1211-1222; Nalbandian, A. et al. (2009) *Clin. Exp. Immunol.* 157, 209-215; Pernis, A. B., (2009) *J. Intern. Med.* 265, 644-652; Valencia, X. et al. (2007) *J. Immunol.* 178, 2579-2588; Zhao, X. F. et al. (2010) *Mol. Biol. Rep.* 37, 81-85) several studies suggest a possible $T_H2$ contribution. (Akahoshi, M. et al. (1999) *Arthritis Rheum.* 42, 1644-1648; Heine, G. et al. (2002) *Nephrol. Dial. Transplant.* 17, 1790-1794; Shimizu, S. et al. (2005) *J. Immunol.* 175, 7185-7192). Given that SLE is a disease with a strong humoral response, (Tiller, T. et al. (2007) *Immunity* 26, 205-213; Tsuiji, M. et al. (2006) *J. Exp. Med.* 203, 393-400) it seems reasonable that SLE may have a $T_H2$ component, as increases in IgE concentration and the presence of autoreactive IgE in the sera of some people with SLE, without any associated increased atopy or allergy, have been reported. (Atta, A. M. et al. (2004) *Braz. J. Med. Biol. Res.* 37, 1497-1501).

It has been previously reported that $Lyn^{-/-}$ mice develop a strong and constitutive $T_H2$ skewing in early life and show exacerbated responses to $T_H2$ challenges. (Odom, S. et al. (2004) *J. Exp. Med.* 199, 1491-1502; Charles, N. et al. (2009) *Immunity* 30, 533-543; Beavitt, S. J. et al. (2005) *J. Immunol.* 175, 1867-1875). In late life, $Lyn^{-/-}$ mice develop an autoimmune disease that mimics some of the features of human SLE. (Hibbs, M. L. et al. (1995) *Cell* 83, 301-311; Nishizumi, H. et al. (1995) *Immunity* 3, 549-560; Yu, C. C. et al. (2001) *Curr. Biol.* 11, 34-38). $Lyn^{-/-}$ mice have circulating autoantibodies to dsDNA and ANA. Glomerular deposition of circulating immune complexes (CICs) in these mice results in kidney damage and ultimately in death. Notably, a genetic association of LYN with SLE, in a European-American population, was recently reported. (Lu, R. et al. (2009) *Genes Immun.* 10, 397-403). Additionally, B cells from some individuals with SLE express reduced levels of Lyn kinase. (Liossis, S. N. et al. (2001) *J. Investig. Med.* 49, 157-165). Thus, $Lyn^{-/-}$ mice provide a reasonable model to explore the influence of a $T_H2$ environment on the development of lupus-like nephritis.

The present studies address the question of whether the $T_H2$ skewing of $Lyn^{-/-}$ mice functions in the development of late-life lupus-like nephritis and whether similar characteristics are seen in people with SLE. As reported in more detail below, the $T_H2$ phenotype functions in the development of lupus-like nephritis in $Lyn^{-/-}$ mice and is also associated with lupus nephritis in human SLE. Thus, basophils and self-reactive IgE are key components in the development of autoantibody-mediated kidney disease. Importantly, decreases in autoreactive IgE were associated with decreased lupus nephritis, and in the absence of autoreactive IgE, the production of autoantibodiies was greatly decreased, and mice showed normal kidney function. Accordingly, in one embodiment, the invention provides methods of using anti-IgE agents (e.g., antibiotics, such as omalizumab (Xolair) for the treatment or prevention of lupus, lupus nephritis, other lupus-related disorders, and other autoimmune disorders. In another embodiment, the invention provides methods of treating or preventing lupus, lupus nephritis and other lupus-related disorders by depleting basophils in a subject that has lupus, lupus nephritis, or a lupus-related disorder.

Omalizumab and Other Antibodies

Antibodies that act as IgE antagonists (e.g., antibodies rhuMAb-E25 omalizumab (see Finn et al., 2003 J Allergy Clin Immuno 111(2):278-284; Corren et al., 2003 J Allergy Clin Immuno 111(1):87-90; Busse and Neaville, 2001 Curr Opin Allergy Clin Immuno 1(1):105-108; and Tang and Powell, 2001, Eur J Pediatr 160(12): 696-704) are particularly useful in the methods of the invention. In one embodiment, antibodies that selectively bind autoreactive IgE are useful in the methods of the invention. In particular embodiments, the invention provides methods of using omalizumab for the treatment of lupus, lupus nephritis, other lupus-related disorders, and other autoimmune disorders.

Omalizumab is a monoclonal anti-IgE antibody that reduces free IgE concentrations and promotes downregulation of IgE receptors on basophils. Omalizumab inhibits the binding of IgE to the high-affinity IgE receptor FcεRI. IgE plays a role in allergic disease by causing the release of histamine and other inflammatory mediators from mast cells. Omalizumab binds to and neutralizes circulating IgE by preventing IgE from binding to its high-affinity mast-cell receptor. By steric hindrance, omalizumab also prevents binding to the low affinity mast cell receptor. Omalizumab and methods for administering omalizumab are described, for example, in U.S. Pat. No. 6,267,958 and in the following publications: Finn et al. J Allergy Clin Immunol. 2003; 111:278-284; Holgate et al., Curr Med Res Opin. 2001; 17:233-240; Johansson et al., Ann Allergy Asthma Immunol. 2002; 89:132-138, each of which is incorporated herein by reference. Omalizumab is typically administered subcutaneously. Dosages vary from 75 mg to 500 mg per dose. In certain embodiments, the dose is 75, 100, 150, 200, 250, 300, 350, 375, 400, 450, or 500 mg per dose. A dose of omalizumab can be administered once or more per week, or may be administered less frequently. For example, any of the aforementioned dosages may be administered once every one, two, three, four, six, eight, or ten weeks. In certain embodiments, omalizumab is administered every 4 weeks at 150 mg or 300 mg per dose, or every 2 weeks at 225 mg, 300 mg, or 375 mg per dose.

Other antibodies useful in the invention are those that modulate IgE signaling, basophil activation, or basophil numbers. In one embodiment, antibodies directed to IL-5 Receptor can be used to reduce or deplete basophils. Methods of preparing antibodies are well known to those of ordinary skill in the science of immunology. As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fc fragment of intact antibody, clear more rapidly from the circulation, and may have less non-specific tissue binding of an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

Unconventional antibodies include, but are not limited to, nanobodies, linear antibodies (Zapata et al., Protein Eng. 8(10): 1057-1062, 1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody since small molecules of ~60-100 kDa in size provide faster blood clearance and rapid tissue uptake See Power et al., (Generation of recombinant multimeric antibody fragments for tumor diagnosis and therapy. Methods Mol Biol, 207, 335-50, 2003); and Wu et al. (Anti-carcinoembryonic antigen (CEA) diabody for rapid tumor targeting and imaging. Tumor Targeting, 4, 47-58, 1999).

Various techniques for making and unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments by the use of single-chain Fv (sFv) diners is described by Gruber et al. (*J. Immunol.* 152:5368, 1994). Trispecific antibodies are described by Tutt et al. (*J. Immunol.* 147:60, 1991). Single chain Fv polypeptide antibodies include a covalently linked VH::VL heterodimer which can be expressed from a nucleic acid including $V_H$- and $V_L$-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

In one embodiment, an antibody that binds self-reactive IgE is monoclonal. Alternatively, the anti-IgE antibody is a polyclonal antibody. The preparation and use of polyclonal antibodies are also known the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing soluble polypeptides, or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding human IgE or immunogenic fragments thereof, can be provided to the host in a delivery vehicle that is taken up by immune cells of the host. The cells will in turn express the human IgE thereby generating an immunogenic response in the host. Alternatively, nucleic acid sequences encoding human IgE or immunogenic fragments thereof, can be expressed in cells in vitro, followed by isolation of the human IgE and administration of the IgE to a suitable host in which antibodies are raised.

Alternatively, antibodies against self-reactive IgE may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Inhibitory Nucleic Acids

Inhibitory nucleic acid molecules are those oligonucleotides that inhibit the expression or activity of IgE or decrease basophil activity for the treatment of lupus, lupus nephritis, lupus-related disorders, and other autoimmune disorders. Such oligonucleotides include single and double stranded nucleic acid molecules (e.g., DNA, RNA, and analogs thereof) that bind a nucleic acid molecule that encodes IgE (e.g., antisense molecules, siRNA, shRNA) as well as nucleic acid molecules that bind directly to a IgE polypeptide to modulate its biological activity (e.g., aptamers).

Ribozymes

Catalytic RNA molecules or ribozymes that target an antisense IgE sequence of the present invention can be used to inhibit expression of a IgE nucleic acid molecule in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

Accordingly, the invention also features a catalytic RNA molecule that includes, in the binding arm, an antisense RNA having between eight and nineteen consecutive nucleobases. In preferred embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

siRNA

Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference). The therapeutic effectiveness of an sirNA approach in mammals was demonstrated in vivo by McCaffrey et al. (Nature 418: 38-39.2002).

Given the sequence of a target gene, siRNAs may be designed to inactivate that gene. Such siRNAs, for example, could be administered directly to an affected tissue, or administered systemically. The nucleic acid sequence of an Par1 gene can be used to design small interfering RNAs (siRNAs). The 21 to 25 nucleotide siRNAs may be used, for example, as therapeutics to treat lupus.

The inhibitory nucleic acid molecules of the present invention may be employed as double-stranded RNAs for RNA interference (RNAi)-mediated knock-down of IgE expression. In one embodiment, IgE expression is reduced in a B cell. RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). The introduction of siRNAs into cells either by transfection of dsRNAs or through expression of siRNAs using a plasmid-based expression system is increasingly being used to create loss-of-function phenotypes in mammalian cells.

In one embodiment of the invention, a double-stranded RNA (dsRNA) molecule is made that includes between eight and nineteen consecutive nucleobases of a nucleobase oligomer of the invention. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

Delivery of Nucleobase Oligomers

Naked inhibitory nucleic acid molecules, or analogs thereof, are capable of entering mammalian cells and inhibiting expression of a gene of interest. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Polynucleotide Therapy

The invention also provides methods for delivering vectors which encode polypeptides that block IgE signaling. Polynucleotide therapy featuring a polynucleotide encoding an inhibitory nucleic acid molecule targeting an IgE protein, variant, or fragment thereof is one therapeutic approach for treating lupus. Expression of such proteins in a subject is expected to promote the selective elimination of IgEs. Such nucleic acid molecules can be delivered to cells of a subject having lupus. In another embodiment, the vector encodes a soluble polypeptide comprising the extracellular fragment of FcεR. The nucleic acid molecules may be delivered to the cells of a subject in a form in which they can be taken up so that therapeutically effective levels of the inhibitory nucleic acid molecule thereof can be produced.

Expression vectors encoding an inhibitory nucleic acid molecule targeting IgE may be administered for global expression or may be used for the transduction of selected tissues. Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding an anti-IgE protein, variant, or a fragment thereof, can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). Most preferably, a viral vector is used to administer an anti-IgE polynucleotide systemically.

Non-viral approaches can also be employed for the introduction of therapeutic to a cell of a patient requiring inhibition of lupus. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Another therapeutic approach included in the invention involves administration of a recombinant therapeutic, such as a recombinant an anti-IgE protein, variant, or fragment thereof, either directly to the site of a potential or actual disease-affected tissue or systemically (for example, by any conventional recombinant protein administration technique). The dosage of the administered protein depends on a number of factors, including the size and health of the individual patient. For any particular subject, the specific dosage regimes should be adjusted over time according to the individual need and the professional judgment of the person administering or supervising the administration of the compositions.

Screens for Agents that Inhibit IgE or Basophil Activity

As reported herein below, IgE and basophil activity are associated with lupus, lupus nephritis, other lupus-related disorders, and other autoimmune disorders. Given that subjects having increased self-reactive IgE and basophil activity are at risk of developing lupus nephritis, agents that selectively reduce the number or activity of basophils or inhibit IgEs are useful for the treatment of lupus, lupus nephritis, other lupus-related disorders, and other autoimmune disorders. If desired, agents that decrease the expression or biological activity of IgEs and/or basophils are tested for efficacy in enhancing the selective reduction of circulating immune complexes (CICs). In one example, a candidate compound is added to the culture medium of cells (e.g., basophils) prior to, concurrent with, or following the addition of an agent that activates basophils (e.g. IgE). The activation or degranulation of the basophils is then measured using standard methods (e.g., measuring CD62 Ligand expression). The level of basophil activation measured in the presence of the candidate agent is compared to the level measured in a corresponding control culture that did not receive the candidate agent. Alternatively, the agent's ability to block IgE binding to basophils is measured. In another embodiment, an in vitro assay can be used to measure IgE binding to its receptor in a screen for compounds or agents that modulate or inhibit IgE binding to its receptor. A compound that inhibits basophil activation, blocks IgE receptor binding, or reduces IgE biding to basophils is identified as useful in the invention; such a candidate compound may be used, for example, as a therapeutic to prevent, delay, ameliorate, stabilize, or treat a disease or disorder associated with lupus.

An agent isolated by this method (or any other appropriate method) may, if desired, be further purified (e.g., by high performance liquid chromatography). In addition, such candidate agents may be tested for their ability to modulate IgE binding or basophil activation in animal models. In other embodiments, the agent's activity is measured by identifying a decrease in IgE or CICs. Agents isolated by this approach may be used, for example, as therapeutics to treat or prevent lupus in a subject.

Candidate agents include organic molecules, peptides, peptide mimetics, polypeptides, and nucleic acid molecules. Each of the sequences listed herein may also be used in the discovery and development of a therapeutic compound for the treatment of lupus. The encoded protein, upon expression, can be used as a target for the screening of drugs. Additionally, the DNA sequences encoding the amino terminal regions of the encoded protein or Shine-Delgarno or other translation facilitating sequences of the respective mRNA can be used to construct sequences that promote the expression of the coding sequence of interest. Such sequences may be isolated by standard techniques (Ausubel et al., supra). Small molecules of the invention preferably have a molecular weight below 2,000 daltons, more preferably between 300 and 1,000 daltons, and most preferably between 400 and 700 daltons. It is preferred that these small molecules are organic molecules.

The invention also includes novel agents identified by the above-described screening assays. Optionally, such agents are characterized in one or more appropriate animal models to determine the efficacy of the compound for the treatment or prevention of lupus. Desirably, characterization in an animal model can also be used to determine the toxicity, side effects, or mechanism of action of treatment with such a compound. Furthermore, a novel agent identified in any of the above-described screening assays may be used for the treatment of lupus in a subject. Such agents are useful alone or in combination with other conventional therapies known in the art.

Test Agents and Extracts

In general, agents capable of modulating basophil activity and/or IgE binding are identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or agent is not critical to the screening procedure(s) of the invention. Agents used in screens may include known agents (for example, known therapeutics used for other diseases or disorders (e.g., omalizumab). Alternatively, virtually any number of unknown chemical extracts or agent can be screened using the methods described herein. Examples of such extracts or agents include, but are not limited to, plant-, fungal-, prokaryotic- or animal-based extracts, fermentation broths, and synthetic agents, as well as modification of existing agents.

Numerous methods are also available for generating random or directed synthesis (e.g., semi-synthesis or total synthesis) of any number of chemical agents, including, but not limited to, saccharide-, lipid-, peptide-, and nucleic acid-based agent. Synthetic compound libraries are commercially available from Brandon Associates (Merrimack, N.H.) and Aldrich Chemical (Milwaukee, Wis.). Alternatively, chemical agent to be used as candidate agent can be synthesized from readily available starting materials using standard synthetic techniques and methodologies known to those of ordinary skill in the art. Synthetic chemistry transformations and protecting group methodologies (protection and deprotection) useful in synthesizing the agent identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Alternatively, libraries of natural agents in the form of bacterial, fungal, plant, and animal extracts are commercially available from a number of sources, including Biotics (Sussex, UK), Xenova (Slough, UK), Harbor Branch Oceanographic Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Libraries of agents may be presented in solution (e.g., Houghten, *Biotechniques* 13:412-421, 1992), or on beads (Lam, *Nature* 354:82-84, 1991), chips (Fodor, *Nature* 364: 555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract of interest is identified, further fractionation of the positive lead extract is necessary to isolate chemical constituents responsible for the observed effect. Thus, the goal of the extraction, fractionation, and purification process is the careful characterization and identification of a chemical entity within the crude extract that alters the transcriptional activity of a gene associated with lupus. Methods of fractionation and purification of such heterogenous extracts are known in the art. If desired, agents shown to be useful as therapeutics for the treatment of lupus are chemically modified according to methods known in the art.

Fostamatinib and Other Pharmaceutical Therapeutics

Agents that act as IgE antagonists (e.g., the small molecule Syk kinase inhibitor Fostamatinib) are particularly useful in the methods of the invention. The invention provides agents that decrease the expression or activity of self-reactive IgE and/or basophils, including agents identified in the above-identified screens, for the treatment of lupus. In one embodiment, the invention provides pharmaceutical agents that inhibit or modulate IgE synthesis or secretion. In another embodiment, a chemical entity discovered to have medicinal value using the methods described herein is useful as a drug or as information for structural modification of existing agent, e.g., by rational drug design. In another embodiment, a small molecule inhibitor of Syk kinase is useful for modulating basophil activity or decreasing basophil numbers. Fostamatinib is an example of a Syk kinase inhibitor that is useful in the claimed methods.

For therapeutic uses, the compositions or agents identified using the methods disclosed herein may be administered systemically, for example, formulated in a pharmaceutically-acceptable carrier. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a lupus therapeutic in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and the clinical symptoms of lupus. Generally, amounts will be in the range of those used for other agents used in the treatment of lupus, although in certain instances lower amounts will be needed because of the increased specificity of the compound. A compound is administered at a dosage that controls the clinical or physiological symptoms of lupus as determined by a diagnostic method known to one skilled in the art, or using any that assay that measures the transcriptional activation of a gene associated with lupus.

Formulation of Pharmaceutical Compositions

The administration of an agent of the invention or analog thereof for the treatment of lupus may be by any suitable means that results in a concentration of the therapeutic that, combined with other components, is effective in ameliorating, reducing, or stabilizing lupus or a symptom thereof. In one embodiment, administration of the agent reduces the binding of self-reactive IgE to basophils. In one embodiment, the agent is administered to a subject for the prevention or treatment of a disease associated with lupus.

Methods of administering such agents are known in the art. The invention provides for the therapeutic administration of an agent by any means known in the art. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). Suitable formulations include forms for oral administration, depot formulations, formulations for delivery by a patch, semisolid dosage forms to be topically or transdermally delivered.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target lupus by using carriers or chemical derivatives to deliver the therapeutic agent to a particular cell type (e.g., basophils) whose function is perturbed in lupus. For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active therapeutic (s), the composition may include suitable parenterally acceptable carriers and/or excipients. The active therapeutic (s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active therapeutic(s) are dissolved or suspended in a parenterally acceptable liquid vehicle.

Controlled Release Parenteral Compositions

Controlled release parenteral compositions may be in the form of suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly (lactic acid), poly(glycolic acid) or poly(ortho esters) or combinations thereof).

Solid Dosage Forms for Oral Use

Formulations for oral use include tablets containing an active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active lupus therapeutic substance). The coating may be applied on the solid dosage form in a similar manner as that described in Encyclopedia of Pharmaceutical Technology, supra.

At least two active lupus therapeutics may be mixed together in the tablet, or may be partitioned. In one example, the first active therapeutic is contained on the inside of the tablet, and the second active therapeutic is on the outside, such that a substantial portion of the second active therapeutic is released prior to the release of the first active therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may be constructed to release the active lupus therapeutic by controlling the dissolution and/or the diffusion of the active substance. Dissolution or diffusion controlled release can be achieved by appropriate coating of a tablet, capsule, pellet, or granulate formulation of agent, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic agent may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Dosage

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used, such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Therapeutic Methods

The present invention provides methods of treating lupus, lupus nephritis, other lupus-related disorders, and other autoimmune disorders by inhibiting or reducing autoreactive IgE or reducing the number or activity of basophils. The methods comprise administering a therapeutically effective amount of a pharmaceutical composition comprising a compound that inhibits or reduces autoreactive IgE or reduces the number or activity of basophils by the methods described herein to a subject (e.g., a mammal such as a human). Thus, one embodiment is a method of treating a subject suffering from or susceptible to lupus. The method includes the step of administering to the subject a therapeutic amount or an amount of a compound herein sufficient to treat the disease or symptom thereof, under conditions such that the disease is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention, which include prophylactic treatment, in general comprise administration of a therapeutically effective amount of the agent herein, such as a compound of the formulae herein to a subject (e.g., animal, human) in need thereof, including a mammal, particularly a human. Such treatment will be suitably administered to subjects, particularly humans, suffering from, having, susceptible to, or at risk for a lupus or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The agent herein may be also used in the treatment of any other disorders in which transcriptional activity may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with lupus, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Kits

The invention provides kits for the treatment or prevention of lupus, lupus nephritis, other lupus-related disorders, and other autoimmune disorders. In one embodiment, the kit includes a therapeutic or prophylactic composition containing an effective amount of an agent of the invention (e.g., omalizumab) in unit dosage form. In some embodiments, the kit comprises a sterile container which contains a therapeutic or prophylactic compound; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the invention is provided together with instructions for administering it to a subject having or at risk of developing lupus. The instructions will generally include information about the use of the composition for the treatment or prevention of lupus. In other embodiments, the instructions include at least one of the following: description of the compound; dosage schedule and administration for treatment or prevention of lupus or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Combination Therapies

Optionally, an agent having therapeutic or prophylactic efficacy may be administered in combination with any other standard therapy for the treatment of lupus; such methods are known to the skilled artisan and described in Remington's Pharmaceutical Sciences by E. W. Martin. If desired, agents of the invention may be administered alone or in combination with a conventional therapeutic useful for the treatment of lupus. Therapeutics useful for the treatment of lupus include, but are not limited to, nonsteroidal anti-inflammatory drugs (NSAIDs), hydroxychloroquine, corticosteroids, cyclophosphamide, azthioprine, methotrexate, mycophenolate, belimumab, dehydroepiandrosterone, rituximab, and others.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Lupus Associated Nephritis is Dependent on IgE and IL-4, but not Mast Cells Consistent with previous results, (Charles, N. et al. (2009) *Immunity* 30, 533-543) basophil-dependent $T_H2$ skewing was still present in aged $Lyn^{-/-}$ mice (FIG. 1a-1d) that develop an SLE-like disease. To study the role of the $T_H2$ environment in the development of the SLE-like phenotype, mice that are deficient in both IgE and Lyn ($Igh-7^{-/-}$; $Lyn^{-/-}$), both IL-4 and Lyn ($Il4^{-/-}$; $Lyn^{-/-}$) or both mast cells and Lyn ($Kit^{W-sh/W-sh}$; $Lyn^{-/-}$) (Charles, N. et al. (2009) *Immunity* 30, 533-543) were used. $Igh-7^{-/-}$; $Lyn^{-/-}$, $Il4^{-/-}$; $Lyn^{-/-}$ and $Kit^{W-sh/W-sh}$; $Lyn^{-/-}$ mice developed a peripheral B cell defect that was comparable to $Lyn^{-/-}$ mice and showed high IgM and IgA concentrations in the serum (FIGS. 2a-2c, 3a-3c, 4a-4f, 5a-5f, and 6a-6f), indicating that IL-4 and IgE were not involved in these abnormalities. The levels of IgE and IgG in $Igh-7^{-/-}$; $Lyn^{-/-}$ and $Il4^{-/-}$; $Lyn^{-/-}$ mice showed a similar trend to the phenotype reported for Igh-7 and 114 single-deficient mice (Kopf, M. et al. (1993) *Nature* 362, 245-248; Oettgen, H. C. et al. (1994) *Nature* 370, 367-370) and differed from the levels in $Lyn^{-/-}$ mice (FIG. 5a-5f). IgE also contributed to the previously reported (Odom, S. et al. (2004) *J. Exp. Med.* 199, 1491-1502) increase in mast cell numbers seen in $Lyn^{-/-}$ mice (FIG. 7a-7g), consistent with a role for IgE in mast cell survival. (Asai, K. et al. (2001) *Immunity* 14, 791-800; Kalesnikoff, J. et al. (2001) *Immunity* 14, 801-811). In contrast, the previously described basophilia in $Lyn^{-/-}$ mice was independent of both IL-4 and IgE (Charles, N. et al. (2009) *Immunity* 30, 533-543) (FIG. 7a-7g).

Figure 8A:
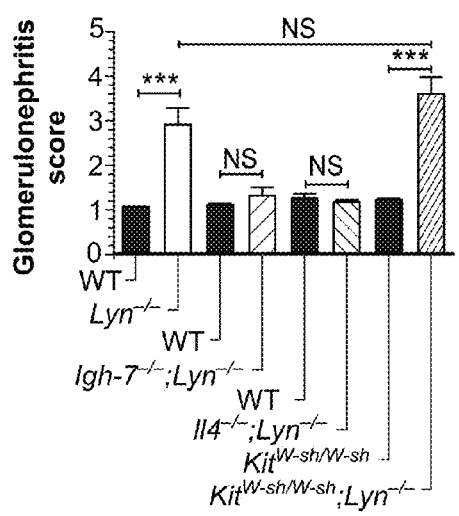
FIGS. 8A, 8B, 8C, and 8D show that lupus-like nephritis in Lyn$^{-/-}$ mice is IL-4 and IgE dependent.
Figure 8D:
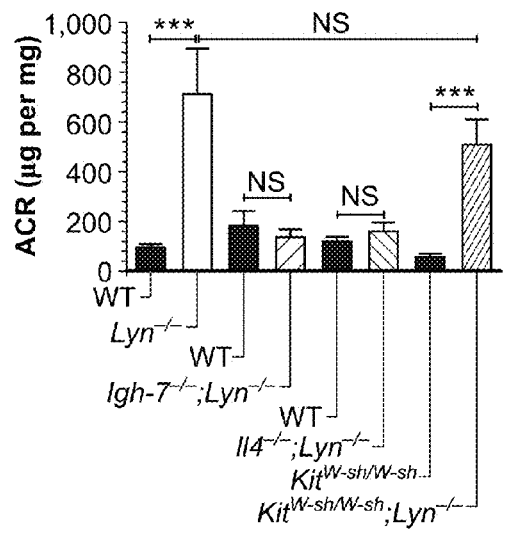
Figure 8B:
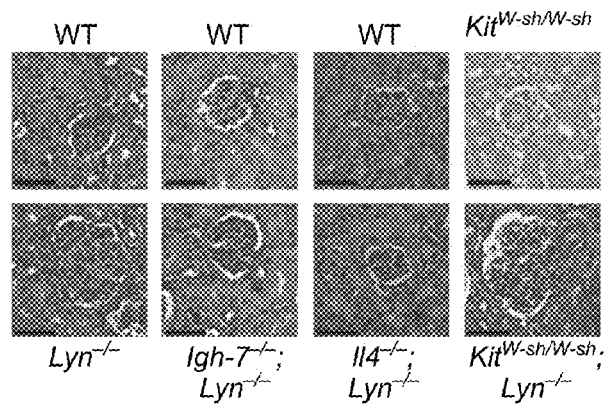
Figure 8C:
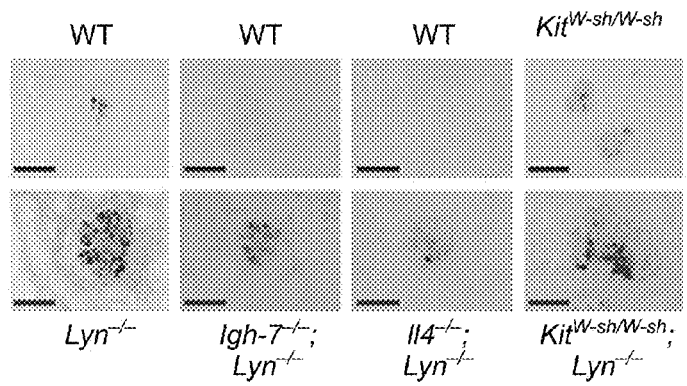
Figure 9:
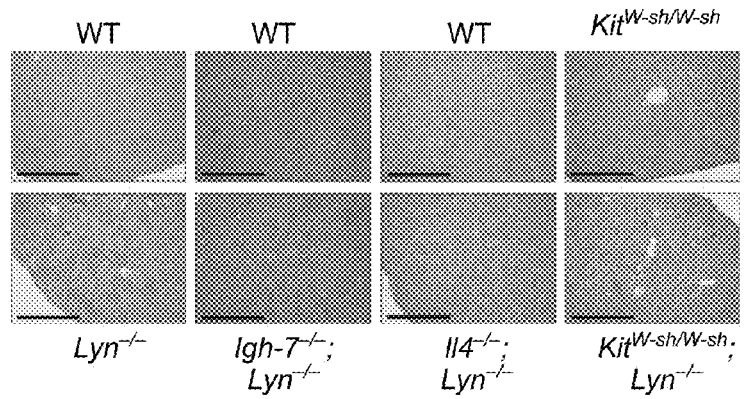
FIG. 9 shows lupus-like glomerulonephritis in Lyn$^{-/-}$ mice is IgE and IL-4 dependent, but mast cell independent. Representative histological kidney sections from 40 weeks old mice of the indicated genotypes with H&E staining. Original magnification ×10. These sections were used to establish the glomerulonephritis score as described in FIG. 8 where original magnification ×40 are shown. Scale bar, 500 μm.
Figure 10A:
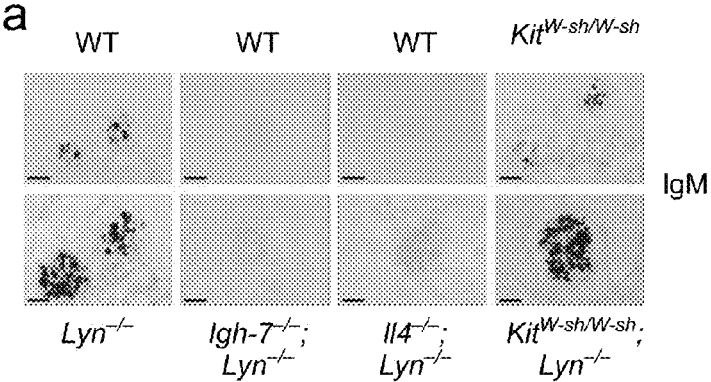
FIGS. 10A, 10B, and 10C show that Glomerular immune complexes depositions in Lyn deficient mice are IgE and IL-4 dependent, but mast cell independent.
Figure 10B:
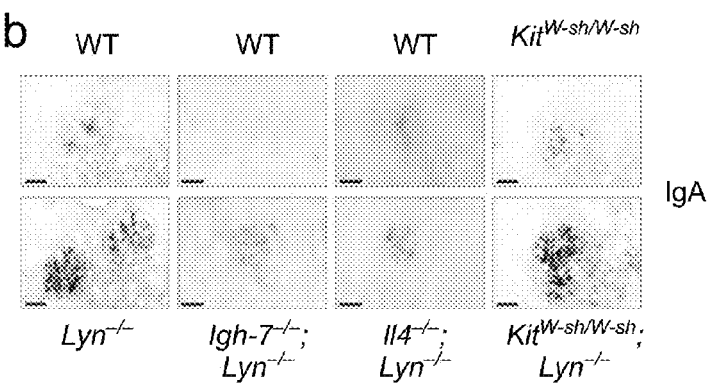
Figure 10C:
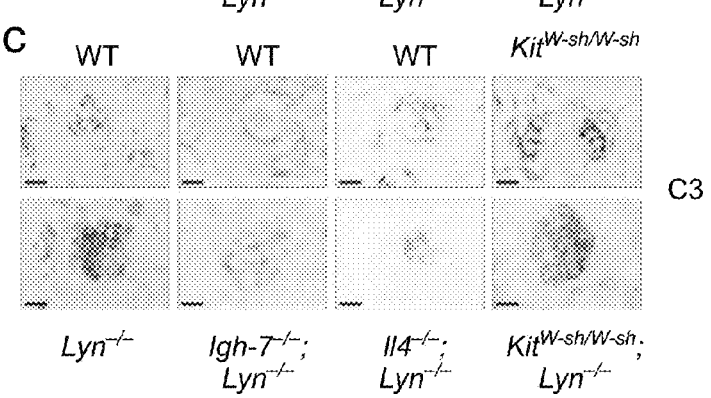

Unlike $Lyn^{-/-}$ and $Kit^{W-sh/W-sh}$; $Lyn^{-/-}$ mice, $Igh-7^{-/-}$; $Lyn^{-/-}$ and $Il4^{-/-}$; $Lyn^{-/-}$ mice did not develop glomerulonephritis (FIGS. 8a, 8b, and 9). Glomerular deposits of circulating immune complexes (CICs) containing IgG (FIG. 8c), IgM, IgA and complement factor 3 (C3) (FIGS. 10a, 10b, and 10c) were markedly reduced in the kidneys of $Igh-7^{-/-}$; $Lyn^{-/-}$ and $Il4^{-/-}$; $Lyn^{-/-}$ mice but were still present in the kidneys of $Kit^{W-sh/W-sh}$; $Lyn^{-/-}$ at comparable levels to $Lyn^{-/-}$ mice (FIGS. 8c, 10a, 10b, and 10c). Kidney function (as measured by the albumin-to-creatinine ratio (ACR) in the urine) was rescued in $Igh-7^{-/-}$; $Lyn^{-/-}$ and $Il4^{-/-}$; $Lyn^{-/-}$ mice, whereas the ACR was elevated to a similar degree in both $Kit^{W-sh/W-sh}$; $Lyn^{-/-}$ and $Lyn^{-/-}$ mice (FIG. 8d). These findings show that the lupus-like nephritis observed in $Lyn^{-/-}$ mice is dependent on IgE and IL-4 but independent of mast cells.

Example 2: Basophils Support Autoreactive Plasma Cells in $Lyn^{-/-}$ Mice

Figure 11B:
FIGS. 11A, 11B, 11C, 11D, 11E, and 11F show that IgE, basophils, and IL-4 regulate autoantibody production in $Lyn^{-/-}$ mice, and that basophils alter the kidney cytokine environment.
Figure 11A:
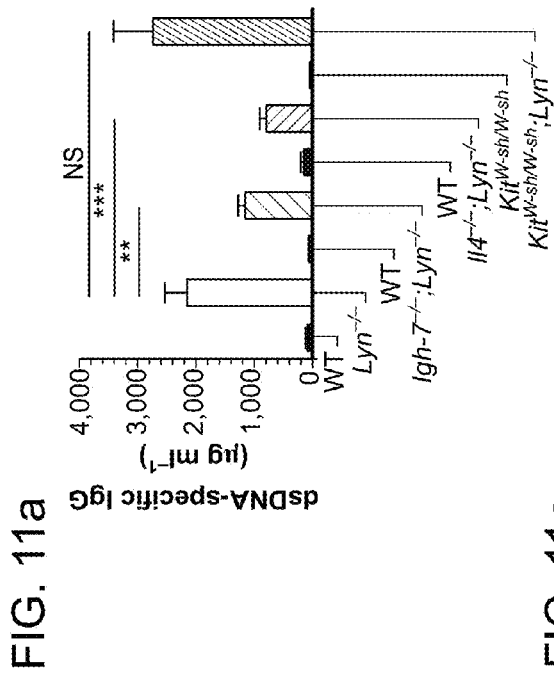
Figure 11D:
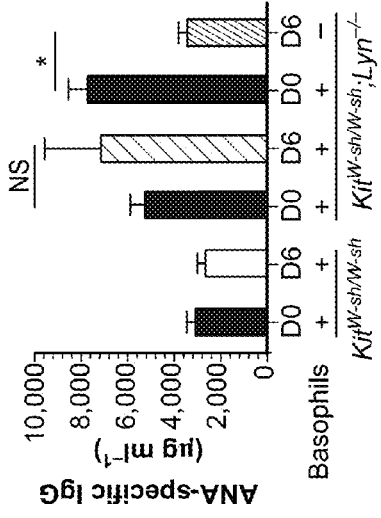
Figure 11C:
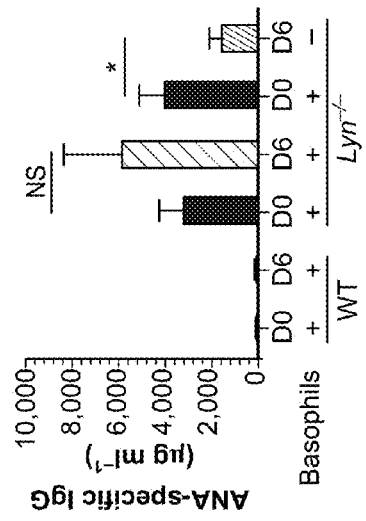
Figure 11F:
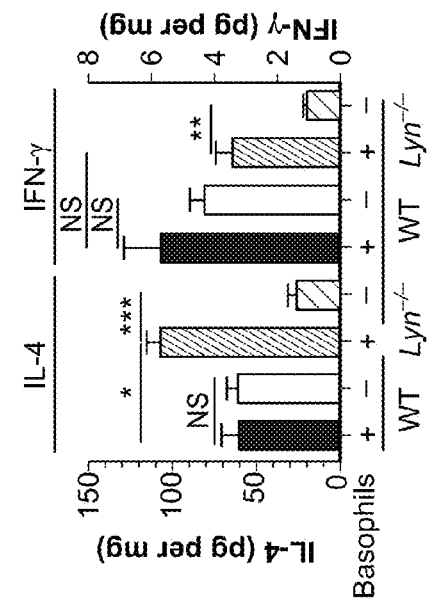
Figure 11E:
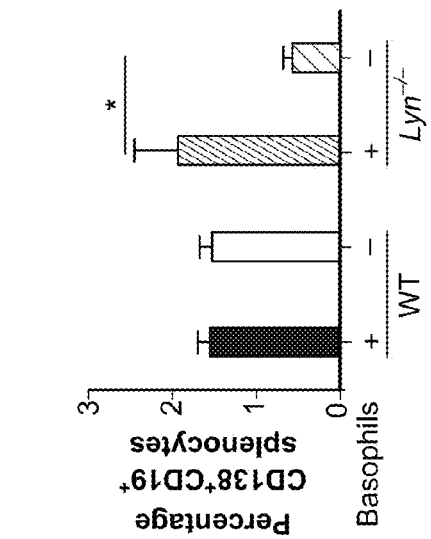
Figure 12B:
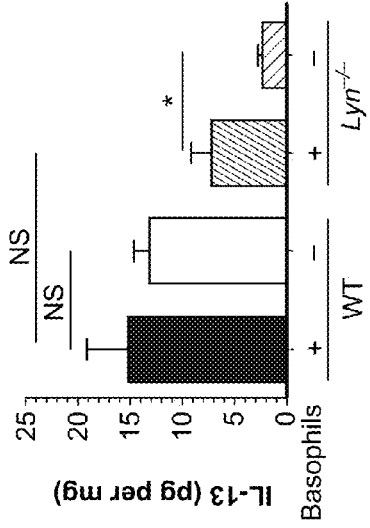
FIGS. 12A, 12B, 12C, and 12D show that Basophil-depletion reduces the pro-inflammatory cytokine environment in the kidney of $Lyn^{-/-}$ mice.
Figure 12A:
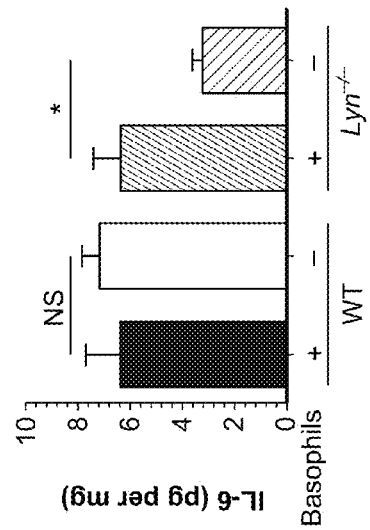
Figure 12D:
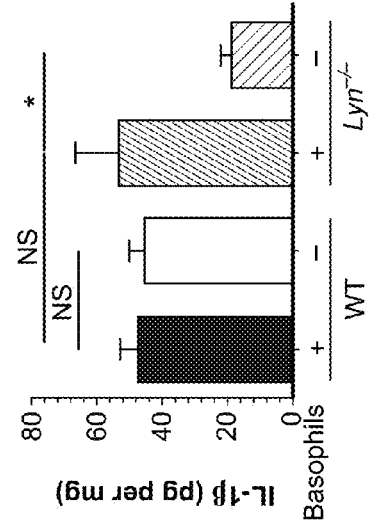
Figure 12C:
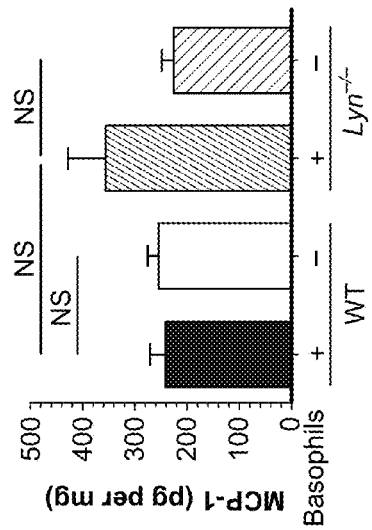

Aged $Lyn^{-/-}$ mice produce large amounts of autoantibodies against dsDNA and nuclear antigens (FIGS. 11a & 11b), which cause the damage seen in the kidney. (Seshan, S. V. & Jennette, J. C. (2009) *Arch. Pathol. Lab. Med.* 133, 233-248; Sinico, R. A. et al. (2009) *Ann. NY Acad. Sci.* 1173, 47-51). Whether the recovery of kidney function in $Igh-7^{-/-}$; $Lyn^{-/-}$ and $Il4^{-/-}$; $Lyn^{-/-}$ mice was associated with a concomitant decrease in autoantibody production and found a two fold decrease in anti-dsDNA and ANA when compared to $Lyn^{-/-}$ and $Kit^{W-sh/W-sh}$; $Lyn^{-/-}$ mice was explored (FIGS. 11a & 11b). Depletion of basophils in aged $Lyn^{-/-}$ mice (>32 weeks) or in younger $Kit^{W-sh/W-sh}$; $Lyn^{-/-}$ mice (~20 weeks) markedly reduced the amount of ANA autoantibodies (FIGS. 11c & 11d). Loss of basophils also decreased the proportion of plasma cells in the spleen (FIG. 11e) and reduced the pro-inflammatory environment in the kidney (FIGS. 11f & 12a-12d). Collectively, the findings show that basophils support plasma cells in the spleen and amplify the production of autoantibodies in an IL-4 and IgE-dependent manner, leading to kidney disease in $Lyn^{-/-}$ mice.

Example 3: $Lyn^{-/-}$ Mice Produce Basophil-Activating Self-Reactive IgE

Figure 13B:
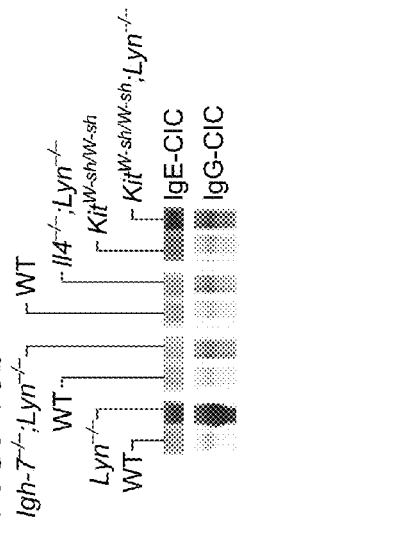
FIGS. 13A, 13B, 13C, and 13D show that autoreactive IgEs and IgE-circulating immune complexes (CICs) are present in the sera of aged $Lyn^{-/-}$ mice.
Figure 13D:
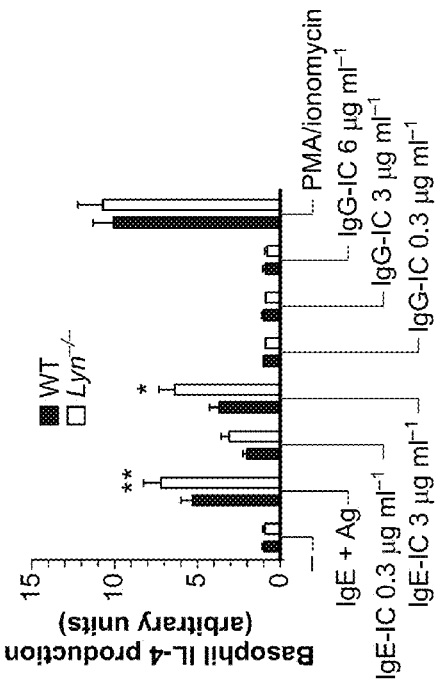
Figure 13A:
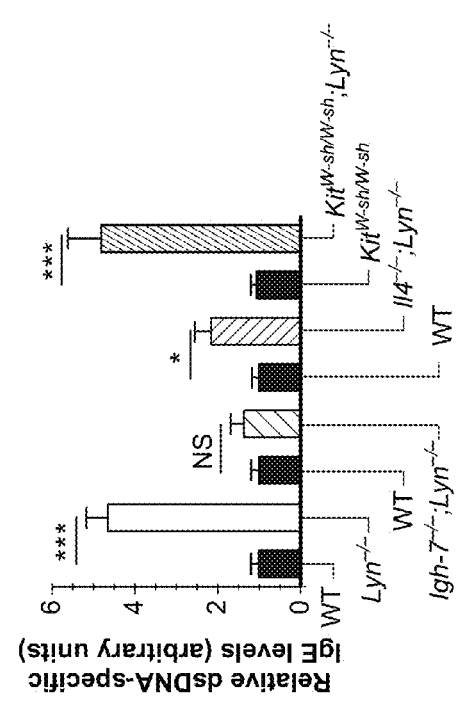
Figure 13C:
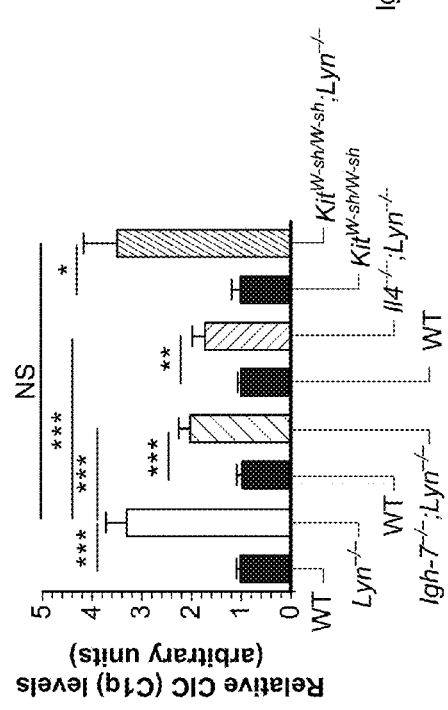
Figure 14A:
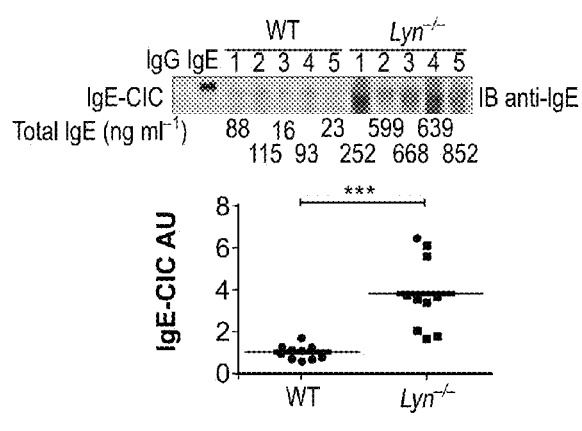
FIGS. 14A, 14B, 14C, 14D, and 14E show that lupus prone $Lyn^{-/-}$ mice contain circulating immune complexes of IgE, IgG, and IgA.
Figure 14D:
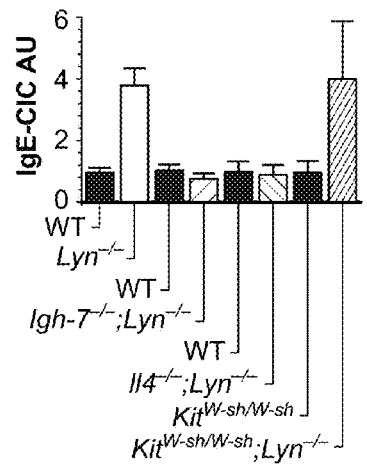
Figure 14B:
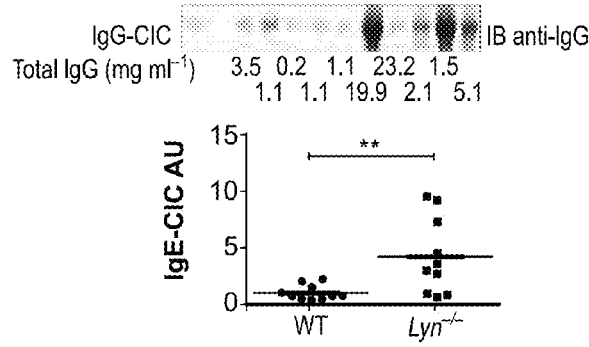
Figure 14E:
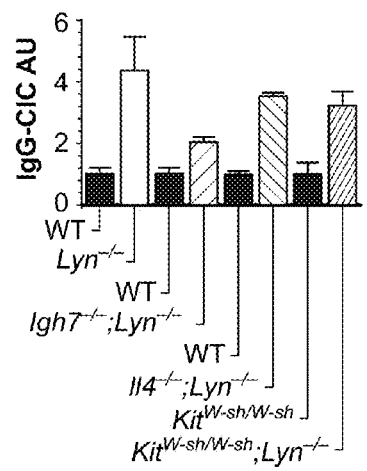
Figure 14C:
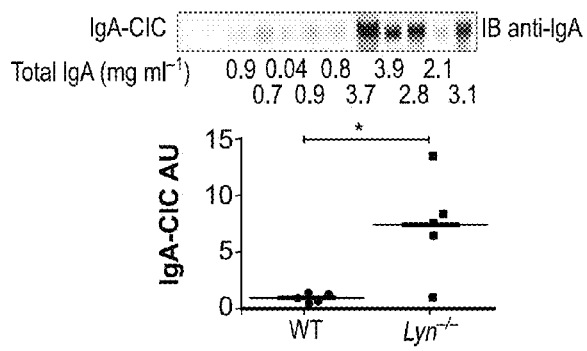

The SLE-like phenotype depends on IgE, thus whether self-reactive IgE could be found in the circulation of these mice, and whether these activate FcεRI-bearing basophils was investigated. Sera from $Lyn^{-/-}$ and $Kit^{W-sh/W-sh}$; $Lyn^{-/-}$ mice had high levels of dsDNA specific IgE (FIG. 13a) and ANA-specific IgE as compared to their wild-type (WT) counterparts. The amount of self-reactive IgEs was reduced in $Il4^{-/-}$; $Lyn^{-/-}$ mice and, as expected, self-reactive IgEs were not detected in $Igh-7^{-/-}$; $Lyn^{-/-}$ mice (FIG. 13a). CICs were purified as previously described (Toran, E. J. & Lee, C. M. (1995) *J. Natl. Med. Assoc.* 87, 693-699) and IgE-containing CICs (IgE-CICs) were found in varying amounts in all of the sera from $Lyn^{-/-}$ and $Kit^{W-sh/W-sh}$; $Lyn^{-/-}$ mice (FIGS. 13b, 14a, and 14d), whereas the sera of $Il4^{-/-}$; $Lyn^{-/-}$ and $Igh-7^{-/-}$; $Lyn^{-/-}$ mice were essentially devoid of IgE-CICs (FIGS. 13b & 14d). IgG-containing (FIG. 13b) and IgM (FIG. 10) and IgA-containing CICs were observed in all of the mutant strains of mice, but a marked reduction in these CICs in $Il4^{-/-}$; $Lyn^{-/-}$ and $Igh-7^{-/-}$; $Lyn^{-/-}$ mice, correlating with the reduced amount of autoantibodies found in these mice were also observed (FIGS. 13c, 14b, 14c, & 14e).

Figure 15A:
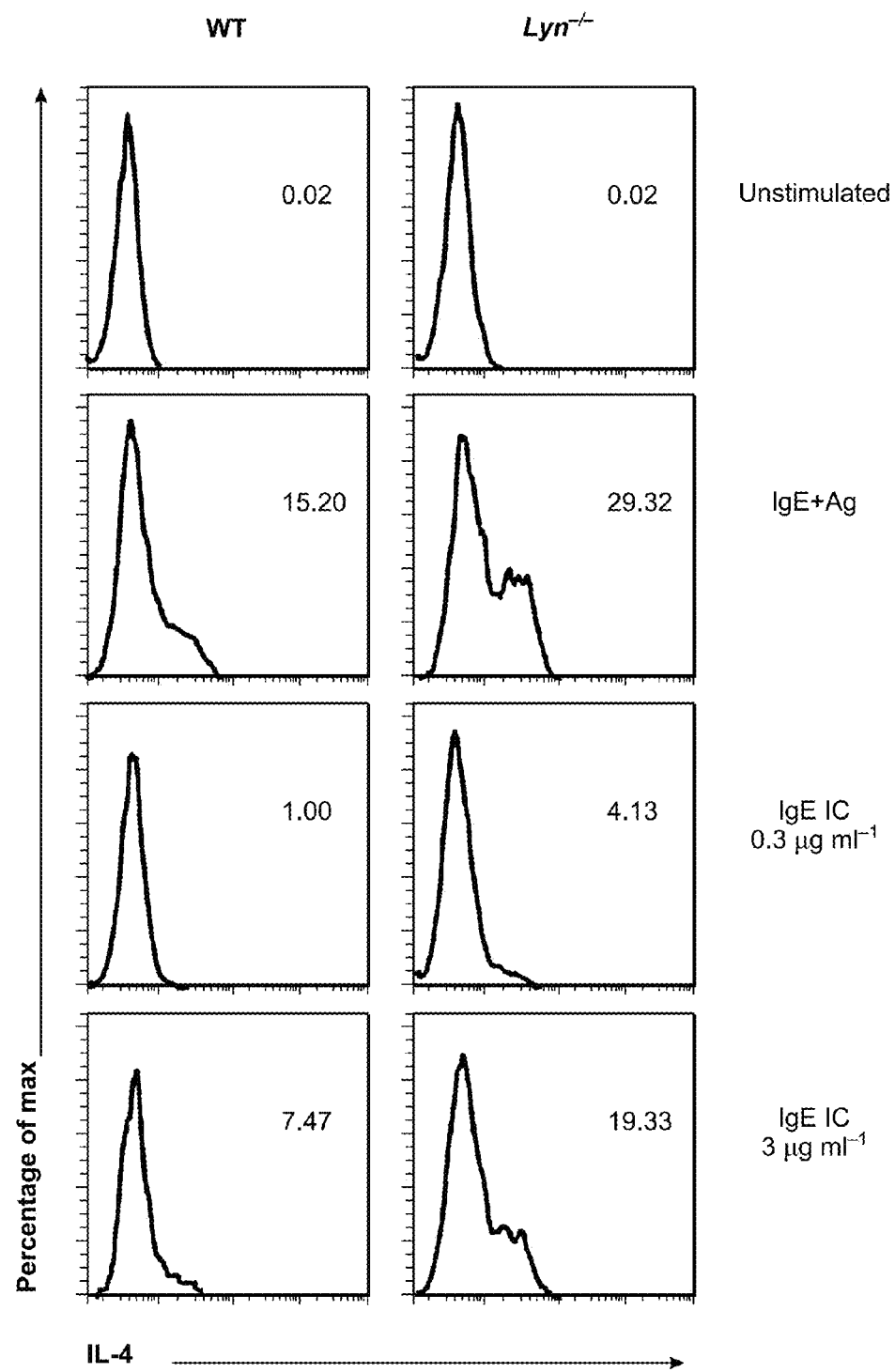
FIGS. 15A, 15B, 15C, and 15D show that IgE-IC, but not IgG-IC, induces cytokine production by basophils.
Figure 15B:
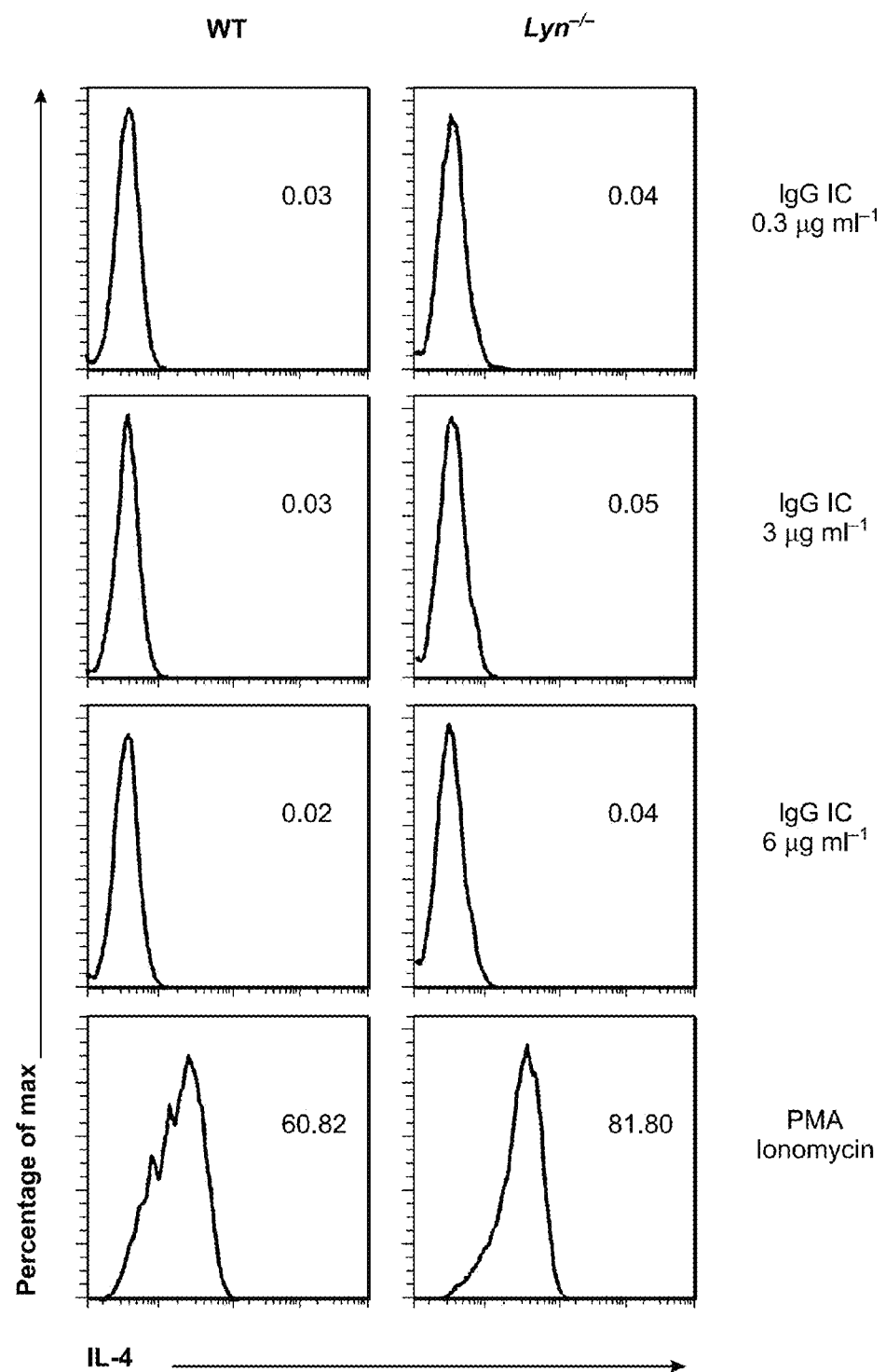
Figure 15C:
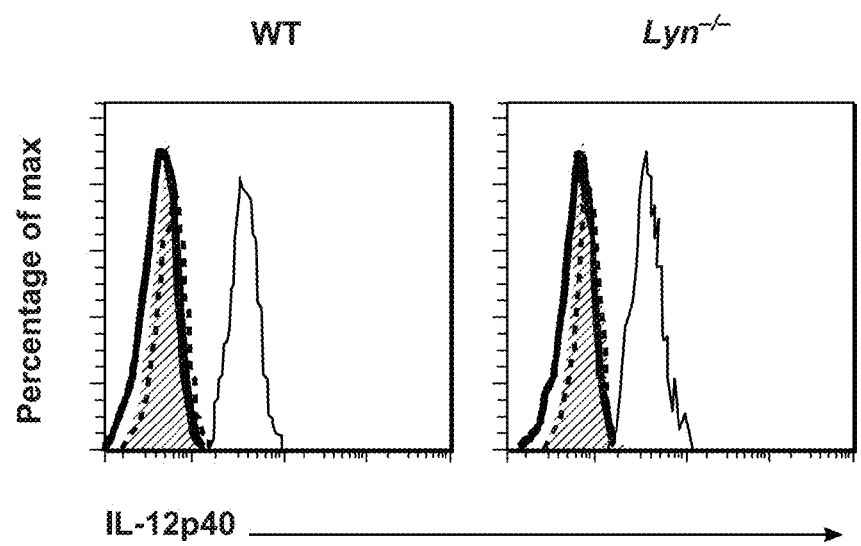
Figure 15D:
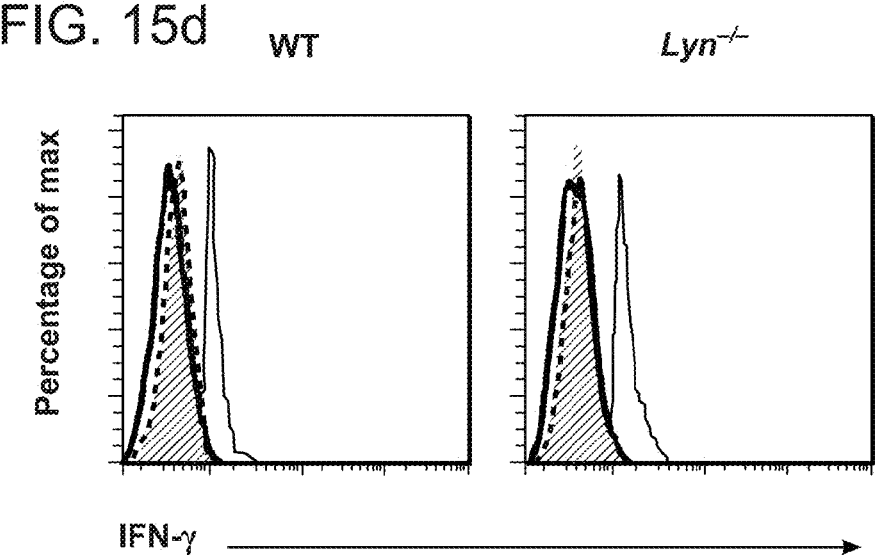

Whether IgE or IgG immune complexes could stimulate basophil IL-4 production was examined. Whereas IgE immune complexes were able to induce IL-4 production by basophils, IgG immune complexes failed to stimulate basophil IL-4 production (FIGS. 13d, 15a, & 15b). Moreover, basophils from $Lyn^{-/-}$ mice showed increased sensitivity to IgE immune complexes as compared to their WT counterparts (FIGS. 13d & 15a). Notably, all of the stimuli tested (phorbol 12-myristate 13-acetate plus ionomycin, dinitrophenyl-specific IgE plus dinitrophenyl-HAS (antigen), IgE immune complexes and IgG immune complexes) failed to induce IL-12 p40 or interferon-γ (IFN-γ) production by basophils from WT or Lyn$^{-/-}$ mice (FIGS. 15c & 15d). These findings demonstrate that the presence of IgE immune complexes (which are present as circulating IgE-CICs in Lyn$^{-/-}$ mice) can lead to basophil activation and selective $T_H2$ cytokine expression.

Example 4: Lyn$^{-/-}$ Basophils Express Immunoregulatory Molecules

Figure 16B:
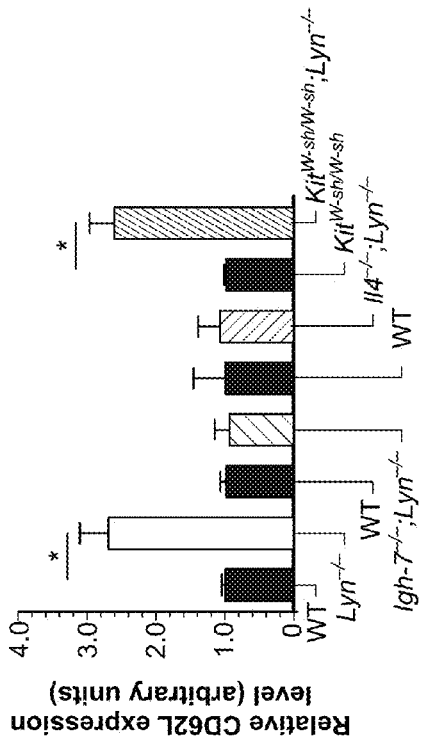
Figure 16D:
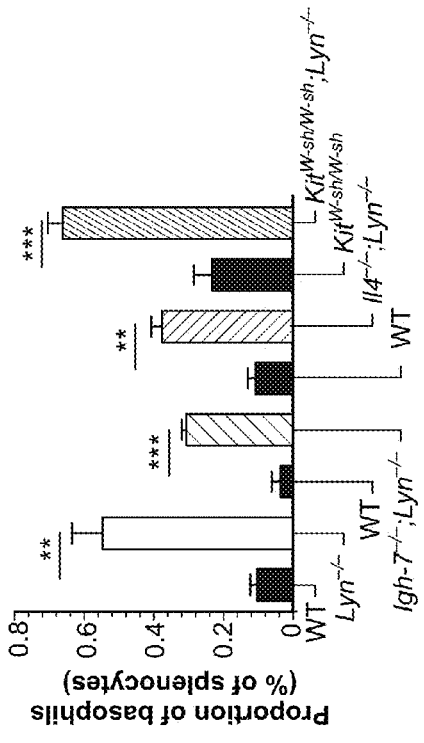
Figure 16A:
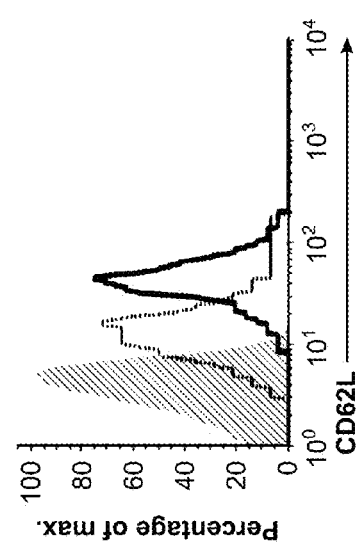
Figure 16C:
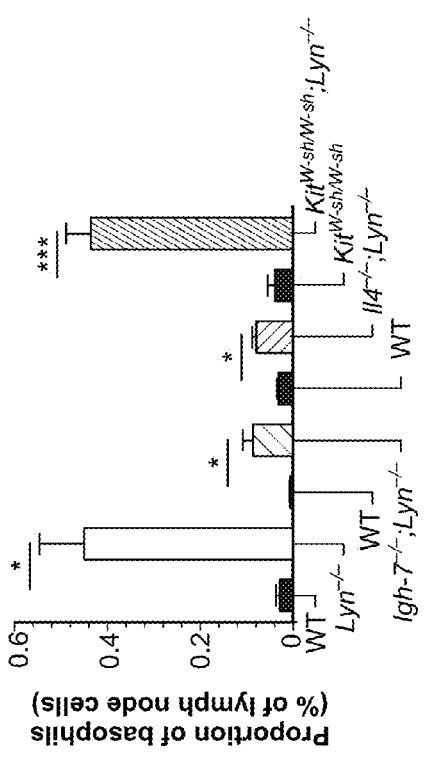

Whether basophils can home to the secondary lymphoid tissues of Lyn$^{-/-}$ mice, where they might influence B and T cell responses was explored. Circulating basophils from Lyn$^{-/-}$ mice showed increased expression of CD62L (L-selectin) (FIG. 16a), which allows for the homing of leukocytes to secondary lymphoid tissues. In the context of Lyn deficiency, the absence of IL-4 or IgE (Il4$^{-/-}$; Lyn$^{-/-}$ and Igh-7$^{-/-}$; Lyn$^{-/-}$ mice), but not of mast cells (Kit$^{W-sh/W-sh}$; Lyn$^{-/-}$ mice), inhibited the expression of CD62L on circulating basophils (FIG. 16b). Lyn$^{-/-}$ mice had high numbers of basophils in both the lymph nodes (cervical and inguinal) and spleen (FIGS. 16c & 16d). In the lymph nodes, the proportion of basophils was markedly reduced when IL-4 or IgE were also absent (Il4$^{-/-}$; Lyn$^{-/-}$ and Igh-7$^{-/-}$; Lyn$^{-/-}$ mice) but not when mast cells where absent (Kit$^{W-sh/W-sh}$; Lyn$^{-/-}$ mice) (FIG. 16c). Some reduction in basophil numbers in the spleen was observed, but it was not as marked as in the lymph nodes (FIG. 16d).

Owing to the basophilia seen in the absence of Lyn, there was no significant difference in the proportion of circulating basophils for any of the studied strains (FIG. 16e). It was also found that lymph node-resident basophils expressed membrane-associated B cell activating factor belonging to the TNF family (BAFF) (FIG. 16f), which was not accounted for by the low amounts of BAFF receptor expressed on these cells, demonstrating the potential of lymph node-resident basophils to influence B cell survival and differentiation. Moreover, both lymph node—(FIG. 16g) and spleen (FIG. 17) resident basophils from Lyn$^{-/-}$ mice showed high MHC II expression. These findings indicate that Lyn$^{-/-}$ basophils upregulate CD62L expression and home to the lymph nodes and spleen, where increased expression of MHC II, (Perrigoue, J. G. et al. (2009) Nat. Immunol. 10, 697-705; Sokol, C. L. et al. (2009) Nat. Immunol. 10, 713-720; Yoshimoto, T. et al. (2009) Nat. Immunol. 10, 706-712) BAFF or both may allow communication with T and B cells.

Example 5: Self-Reactive IgE is Associated with SLE and Lupus Nephritis

Figure 18A:
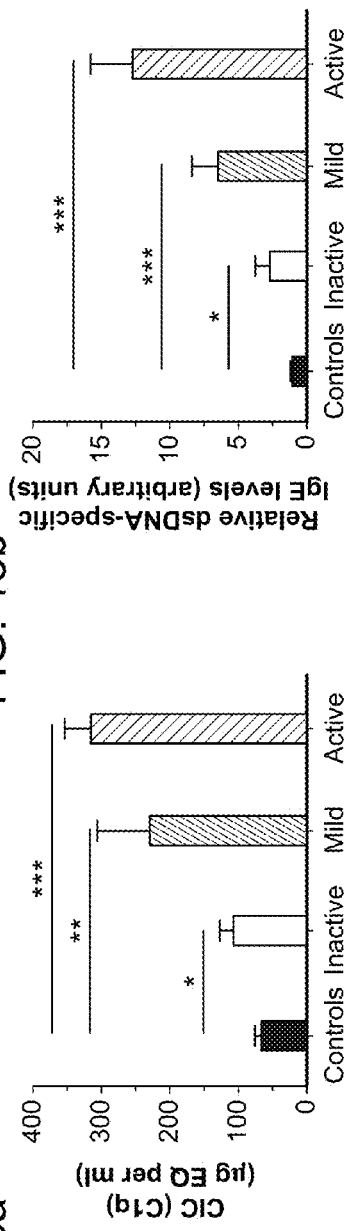
FIGS. 18A, 18B, 18C, and 18D show that dsDNA-specific IgE and IgE-specific IgG are associated with human SLE disease activity and lupus nephritis.
Figure 18B:
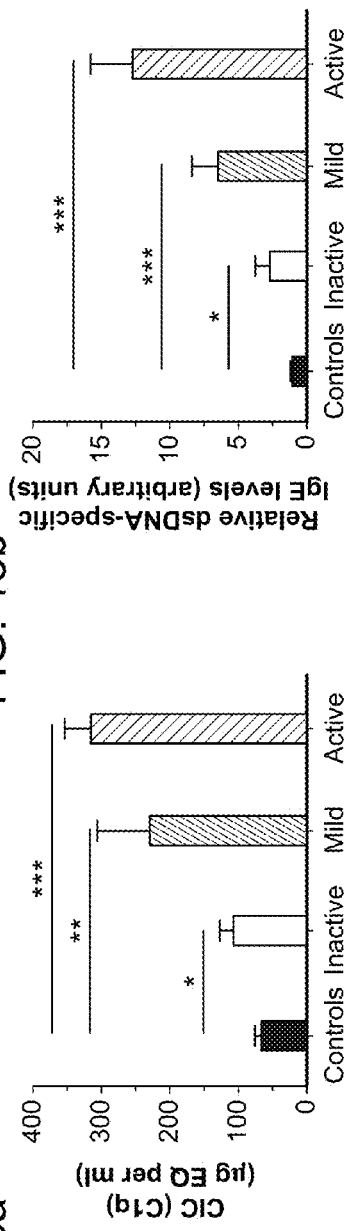

The cohort of subjects with SLE analyzed had large amounts of C1q-reactive CICs that can activate the classical complement pathway (FIG. 18a), a feature previously described for subjects with SLE. (Moser, K. L. et al., (2009) Genes Immun. 10, 373-379; Sinico, R. A. et al. (2009) Ann. NY Acad. Sci. 1173, 47-51). When analyzed relative to disease activity (on the basis of SLE disease activity index (SLEDAI) scores), ((2004) Arthritis Rheum. 50, 3418-3426) C1q-reactive CICs were strongly elevated in mild (SLEDAI score of 1.0-4.0) and active disease (SLEDAI score of >4.0). Subjects with SLE also had self-reactive IgEs recognizing dsDNA, and the levels of these IgEs were associated with increased disease activity (FIG. 18b).

Figure 18C:
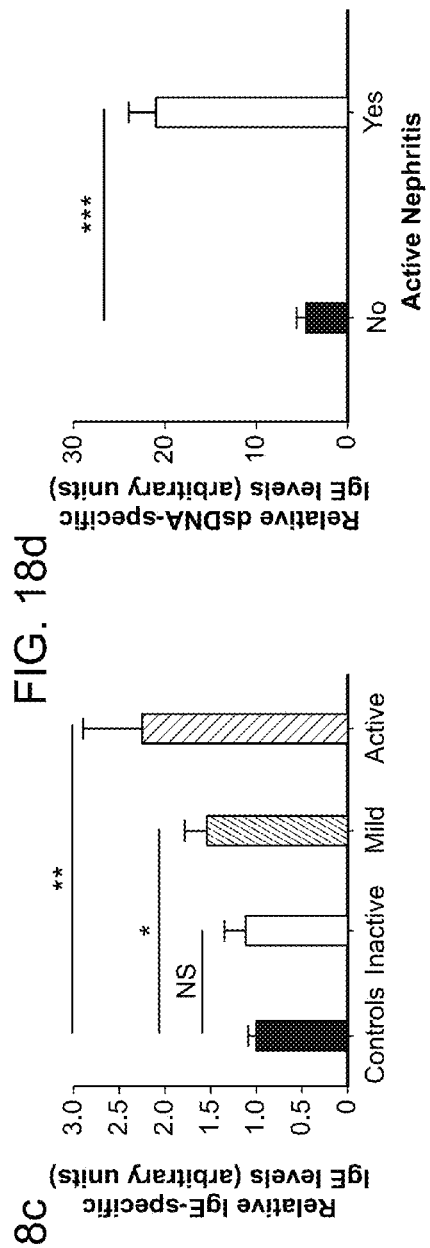
Figure 18D:
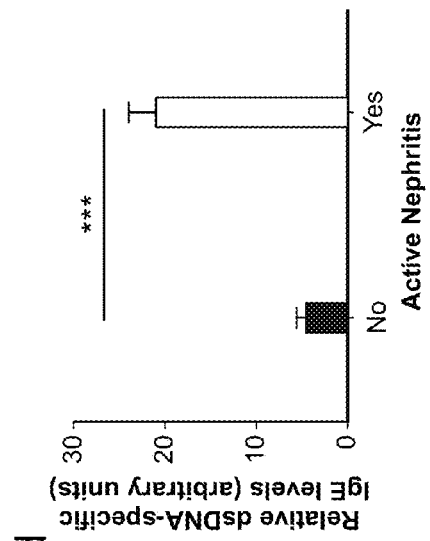
Figure 19A:
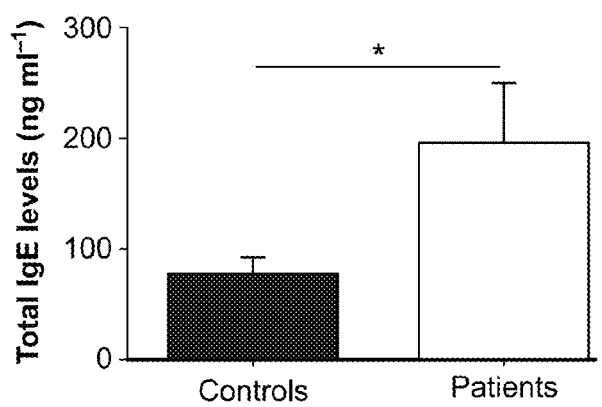
FIGS. 19A, 19B, and 19C show that total IgE levels and dsDNA immunoglobulin subclasses in SLE patients.
Figure 19B:
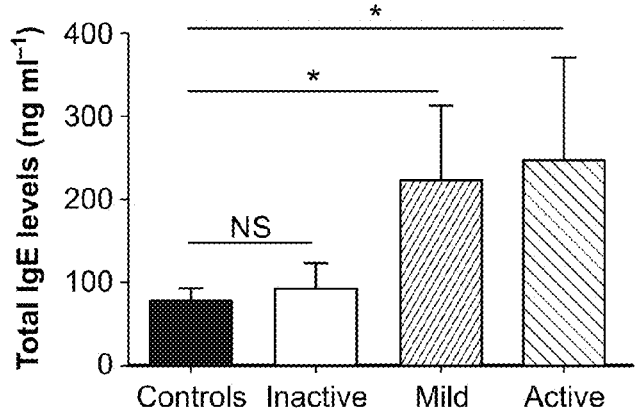
Figure 19C:
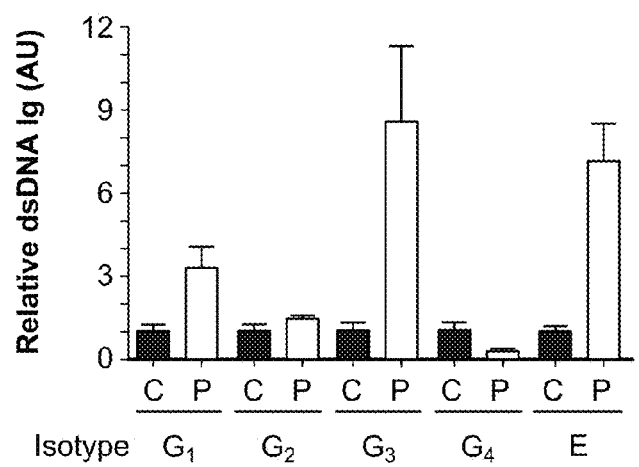

IgGs directed against IgE were also present in the sera of subjects with SLE, with significantly elevated levels in subjects with active disease (FIG. 18c). High levels of dsDNA-specific IgEs were associated with active lupus nephritis (FIG. 18d). Moreover, subjects with SLE had high total IgE levels, which were associated with disease activity, and showed a modest to strong IgG1, IgG3 and IgE autoantibody response (FIGS. 19a, 19b, & 19c). Thus, individuals with SLE have autoantibodies associated with $T_H1$- and $T_H2$-responses, and self-reactive IgEs and IgGs specific for IgE that are associated with increased disease activity and active nephritis.

Example 6: SLE Basophils Express HLA-DR and Home to Lymphoid Tissues

Figure 20A:
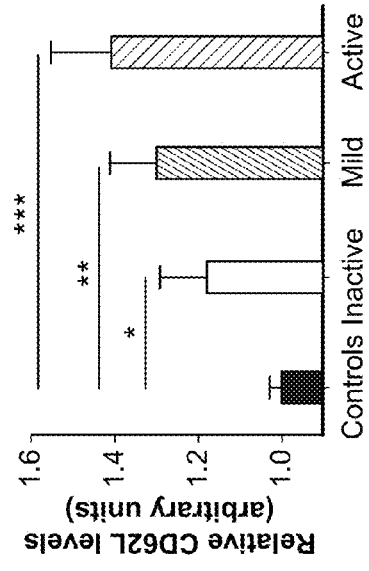
FIGS. 20A, 20B, 20C, 20D, 20E, and 20F show that basophils in individuals with SLE are active, upregulate CD62L and HLA-DR and home to secondary lymphoid organs.
Figure 20B:
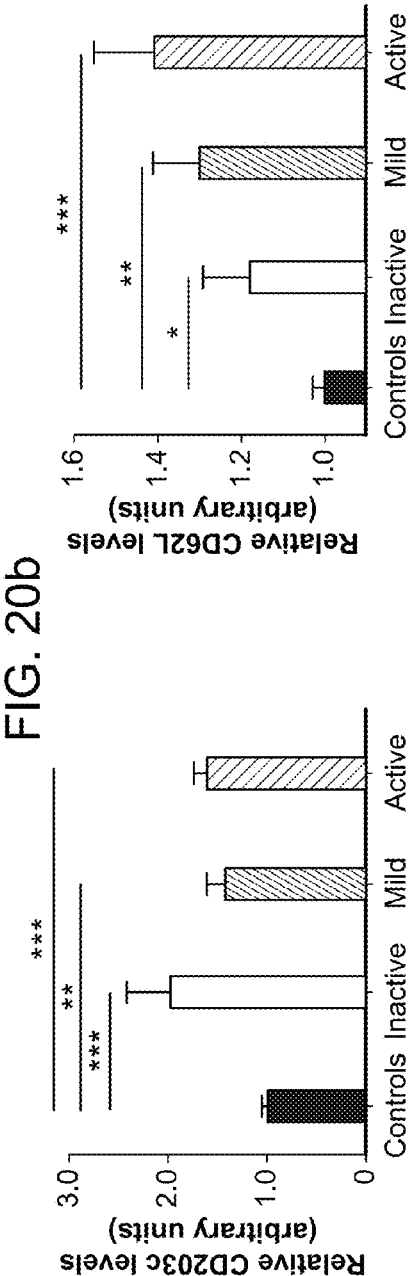
Figure 20C:
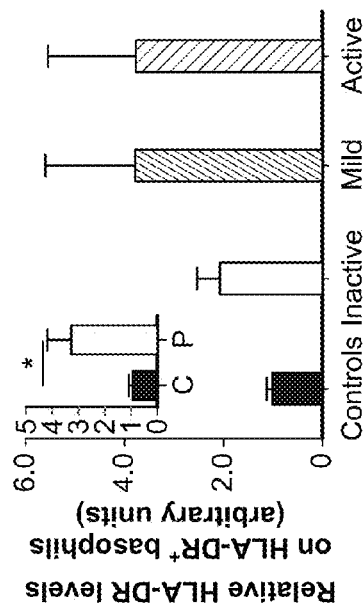

To investigate the activation state of basophils in individuals with SLE, the expression of the marker CD203c was determined, as it is upregulated in activated basophils. (Hauswirth, A. W. et al. (2002) J. Allergy Clin. Immunol. 110, 102-109) All subjects with SLE showed high CD203c expression relative to healthy controls, indicating that their basophils are activated (FIG. 20a). Expression of CD62L (FIG. 20b) and HLA-DR (FIG. 20c) was also elevated on SLE basophils, and were associated with increased disease activity.

Figure 20D:
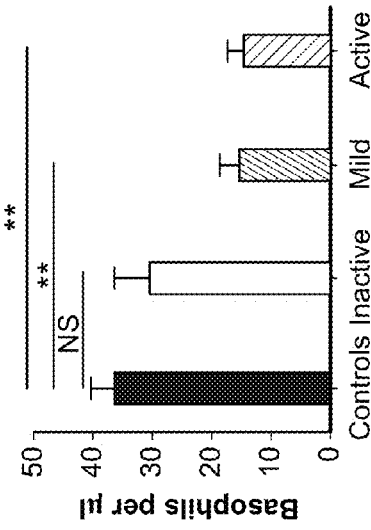
Figure 20E:
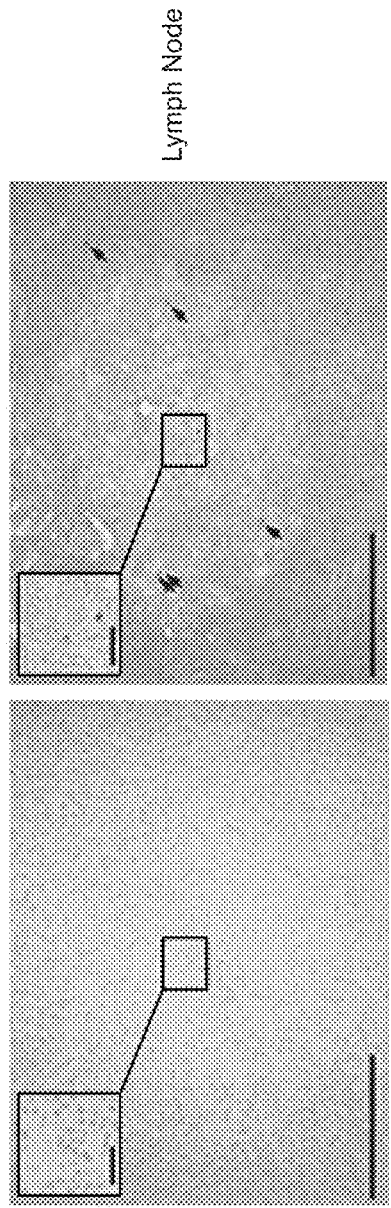
Figure 20F:
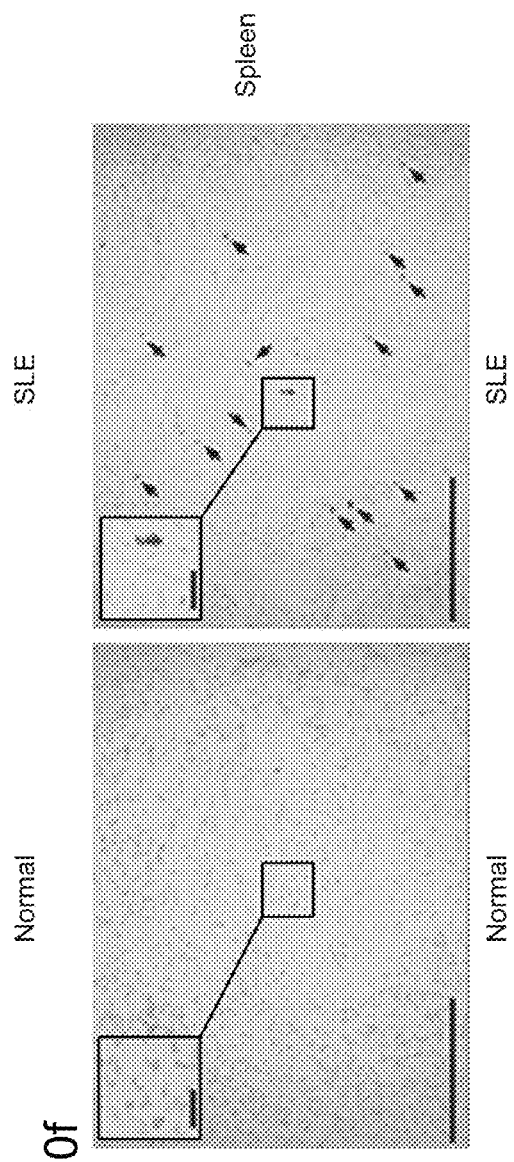

The absolute numbers of basophils in the circulation was decreased in subjects with SLE (FIG. 20d). Although this decrease was associated with immunosuppressive treatment (FIGS. 21a, 21b, 21c, and 21d), immunosuppressive treatment had no effect on the activation state of basophils (as indicated by the presence of HLA-DR). Of note, basophils were found in the lymph nodes and spleen of the two subjects tested with SLE, but not in control subjects without SLE (FIGS. 20e & 20f). The findings suggest that basophils in individuals with SLE are activated, home to secondary lymphoid organs and express the appropriate molecules for antigen presentation. This is associated with the presence of self-reactive IgE in individuals with SLE.

Although SLE has long been considered a B cell disease, self-reactive T cells that promote B cell class switching, (Singh, R. R. et al. (1995) J. Clin. Invest. 96, 2990-2996) and other cell types such as dendritic cells and macrophages, (Kyttaris, V. C. et al. (2005) Curr. Rheumatol. Rep. 7, 469-475; Holmdahl, R. et al. (1991) Autoimmunity 8, 271-280) have also been implicated in the disease, for example, through secretion of factors influencing B cell survival and differentiation, such as BAFF and a proliferation-inducing ligand (APRIL). (Levesque, M. C. (2009) Clin. Exp. Immunol. 157, 198-208) Basophils were found to be contributors to the production of self-reactive antibodies in SLE. The findings in Lyn$^{-/-}$ mice show that depletion of basophils or the absence of IL-4 or IgE caused a marked reduction in autoantibody production and preserves kidney function. This demonstrated that without basophils the levels of autoantibodies are insufficient to cause kidney disease. Thus, basophils function to amplify the preexisting loss of B cell tolerance.

Basophils have long been associated with allergy. (Schroeder, J. T. & MacGlashan, D. W. (1997) J. Allergy Clin. Immunol. 99, 429-433; Mukai, K. et al. (2005) Immunity 23, 191-202). However, the role of basophils in immunity remains unclear. The recent discoveries that basophils can induce $T_H2$ cell differentiation in vivo, (Charles, N. et al. (2009) Immunity 30, 533-543; Sokol, C. L. et al. (2008) Nat.

Immunol. 9, 310-318) amplify humoral memory responses (Denzel, A. et al. (2008) *Nat. Immunol.* 9, 733-742) and present antigen via MHC II, (Perrigoue, J. G. et al. (2009) *Nat. Immunol.* 10, 697-705; Yoshimoto, T. et al. (2009) *Nat. Immunol.* 10, 706-712; Sokol, C. L. et al. (2008) *Nat. Immunol.* 9, 310-318) provide evidence of a role for this cell type in regulating $T_H2$ immunity. In the $Lyn^{-/-}$ mouse model, $T_H2$ skewing is driven by the absence of Lyn kinase in basophils, resulting in upregulation of GATA-3 in these cells and an enhanced production of IL-4 in vivo. (Charles, N. et al. (2009) *Immunity* 30, 533-543). In humans, the preliminary analysis of the amount of Lyn in the basophils of subjects with SLE did not reveal substantial differences relative to healthy controls. However, there is increasing evidence of a role for Lyn kinase in SLE, particularly in populations of European descent. (Lu, R. et al. (2009) *Genes Immun.* 10, 397-403; Liossis, S. N. et al. (2001) *J. Investig. Med.* 49, 157-165).

Of note is the finding that basophils contribute to the production of autoantibodies that cause lupus-like nephritis in the $Lyn^{-/-}$ mice. Activation of these cells caused enhancement of CD62L expression and their accumulation in the lymph nodes of $Lyn^{-/-}$ mice and in subjects with SLE. MHC II expression on mouse and human basophils was increased, and in mice expression of membrane-bound BAFF was observed, similar to what has been described in human basophils after engagement of IgD on their cell surface. (Chen, K. et al. (2009) *Nat. Immunol.* 10, 889-898). Depletion of basophils in $Lyn^{-/-}$ mice decreased the counts of splenic plasma cells and suppressed autoantibody production, which drives lupus nephritis. (Seshan, S. V. & Jennette, J. C. (2009) *Arch. Pathol. Lab. Med.* 133, 233-248; Sinico, R. A. et al. (2009) *Ann. NY Acad. Sci.* 1173, 47-51). Depletion of basophils also reduced the production of IL-1β, IL-4, IL-6, IL-13 and IFN-γ in the kidney of $Lyn^{-/-}$ mice. Thus, a reduction in the proinflammatory milieu in the kidney suggests a possible therapeutic benefit from basophil inactivation or depletion.

These findings show that IgE immune complexes can activate basophils, and removal of self-reactive IgEs that form functional CICs (by deletion of the Igh-7 locus or by eliminating IL-4 production) prevents kidney disease. These IgE-CICs were also associated with lupus nephritis in both $Lyn^{-/-}$ mice and human subjects with SLE. Since circulating IgE levels can be reduced by an existing antiallergy drug, omalizumab, an IgE-specific antibody that lowers circulating IgE levels and decreases FcεRI expression on basophils, (Lin, H. et al. (2004) *J. Allergy Clin. Immunol.* 113, 297-302) this drug would be of therapeutic benefit to patients with SLE with elevated IgE levels. Although in individuals with SLE the association of increased levels of dsDNA-specific IgE with increased disease activity and active lupus nephritis argues for a link between increased $T_H2$ responses and the development of nephritis, it is clear that $T_H1$-mediated responses are also found in this population. The presence of increased circulating IgG1 and IgG3 autoantibodies indicates a strong $T_H1$ component. This demonstrates that direct modulation of the $T_H2$ response, through the use of IL-4 and IL-13 receptor antagonists, (Burmeister Getz et al. (2009) *J. Clin. Pharmacol.* 49, 1025-1036) as a therapeutic strategy could have the unwanted effect of exacerbating disease by shifting toward a $T_H1$ (or possibly $T_H17$) phenotype. Nonetheless, IgE-CICs were not found in the kidneys of $Lyn^{-/-}$ mice, it seems that these CICs do not contribute to the kidney pathology per se but instead play a part in basophil activation. Thus, the strategy of IgE or basophil depletion could avoid complications associated with altering the $T_H1$-$T_H2$ balance.

The view of SLE as a disease with a $T_H2$ component has been controversial. There is considerable evidence for the involvement of $T_H1$ and possibly $T_H17$ cells in SLE, (Akahoshi, M. et al. (1999) *Arthritis Rheum.* 42, 1644-1648; Heine, G. et al. (2002) *Nephrol. Dial. Transplant.* 17, 1790-1794; De Carli, M. et al. (1994) *Autoimmunity* 18, 301-308; Kono, D. H. et al. (2000) *Immunol.* 164, 38-42; Peng, S. L. et al. (1997) *J. Clin. Invest.* 99, 1936-1946), as well as for the alteration or loss of regulatory T cell activity. (Valencia, X. et al. (2007) *J. Immunol.* 178, 2579-2588; Lee, H. Y. et al. (2008) Rheumatology (Oxford) 47, 789-794). Some mouse models where spontaneous genetic mutations or alterations cause lupus-like disease, such as BXSB and MRL-Fas$^{lpr}$ mice, show a $T_H1$ cytokine IFN-γ-dependent disease. Deletion of the gene encoding IFN-γ in mice with these backgrounds was shown to eliminate disease. (Balomenos, D. et al., (1998) *J. Clin. Invest.* 101, 364-371; Kono, D. H. et al. (2000) *Immunol.* 164, 38-42). Humans with SLE showed both $T_H1$ and $T_H2$ responses, and both IgG-CICs and IgE-CICs were associated with increased disease activity. Several studies have suggested that the balance between $T_H1$ and $T_H2$ cell responses may determine the phenotype of lupus nephritis. (Masutani, K. et al. (2001) *Arthritis Rheum.* 44, 2097-2106; Akahoshi, M. et al. (1999) *Arthritis Rheum.* 42, 1644-1648; Heine, G. et al. (2002) *Nephrol. Dial. Transplant.* 17, 1790-1794; Shimizu, S. et al. (2005) *J. Immunol.* 175, 7185-7192; De Carli, M. et al. (1994) *Autoimmunity* 18, 301-308). A strong $T_H1$ response was shown to be associated with diffuse proliferative lupus nephritis, whereas a dominant $T_H2$ response was associated with a membranous lupus nephritis. (Masutani, K. et al. (2001) *Arthritis Rheum.* 44, 2097-2106; Akahoshi, M. et al. (1999) *Arthritis Rheum.* 42, 1644-1648; Heine, G. et al. (2002) *Nephrol. Dial. Transplant.* 17, 1790-1794; Shimizu, S. et al. (2005) *J. Immunol.* 175, 7185-7192; De Carli, M. et al. (1994) *Autoimmunity* 18, 301-308). These observations argue that both $T_H1$ and $T_H2$ responses can contribute to lupus nephritis, but the disease may manifest differently depending on the dominance of one or the other response.

These findings show that basophils and the $T_H2$ environment influence the production of autoantibodies and that depletion of basophils or deletion of the Igh-7 or 114 gene, in the context of Lyn deficiency, causes a reduction in the circulating levels of these self-reactive antibodies. In individuals with SLE, self-reactive IgE was associated with active disease and active lupus. Their basophils were active and were found in the secondary lymphoid tissues, of two tested individuals, where they may influence T and B cell function. Thus, these findings demonstrate that decreasing the circulating levels of self-reactive IgE or the dampening of basophil activity would have therapeutic benefit in lupus nephritis.

Materials and Methods for the Above Described Examples.

Mice.

All mice used in the present study were described previously. (Charles, N. et al. (2009) *Immunity* 30, 533-543). Unless otherwise noted, mice were 32-40-weeks-old and were age-matched for group comparisons. Mice were maintained in specific pathogen-free conditions and used in accordance with NIH guidelines and NIAMS-approved animal study proposal A007-03-01.

Human Subjects.

Samples were collected from adult subjects enrolled in a long-term natural history study of SLE. The study was approved by the Institutional Review Board of NIAMS. All subjects fulfilled the American College of Rheumatology classification criteria for SLE. (Hochberg, M. C. (1997) *Arthritis Rheum.* 40, 1725; Tan, E. M. et al. (1982) *Arthritis Rheum.* 25, 1271-1277). Subject characteristics and lupus activity scoring system are shown in FIG. 22. Control samples were obtained from healthy blood donors. All subjects provided written informed consent.

Antibodies and Flow Cytometry.

Dinitrophenyl-specific mouse IgE was produced as previously described. (Liu, F. T. et al. (1980) *J. Immunol.* 124, 2728-2737). All other antibodies were from commercial sources and are described in FIG. 23. Flow cytometry acquisition was done with a FACSCalibur machine (BD Biosciences) as previously described. (Charles, N. et al. (2009) *Immunity* 30, 533-543). Data analysis was with Flowjo software (Treestar).

In vivo basophil depletion and ex vivo analysis of splenic T cells. In vivo basophil depletion and ex vivo analysis of splenic T cells (CD4$^+$) were previously described. (Charles, N. et al. (2009) *Immunity* 30, 533-543).

Glomerulonephritis, analysis of glomerular deposition of circulating immune complexes and kidney function. Aged (~40-week-old) mice were killed, and kidneys were removed. One kidney was fixed with 10% buffered formalin (Sigma), embedded in paraffin, sectioned and stained with H&E (American Histolabs). The other kidney was placed in a vinyl mold in optimal cutting temperature medium, and the sample was frozen in liquid nitrogen. Four-micrometer-thick frozen sections were fixed in cold acetone, blocked in PBS containing 1% BSA and stained in the same buffer with the specific fluorescein-conjugated antibodies or isotype controls (see FIG. 23 for antibodies used).

For assessment of kidney function the albumin/creatinine ratio (ACR) was determined. Urine was collected from at least ten aged mice per genotype and the albumin concentration was measured with a mouse albumin ELISA (Bethyl laboratories). A creatinine assay (R&D systems) was used to determine urine creatinine concentrations. Results are expressed as ACR inn of albumin per mg of creatinine.

Measurement of autoantibodies, circulating immune complexes and precipitation of circulating immune complexes. Mouse IgG specific for dsDNA, mouse ANA-specific IgG and mouse CICs ((C1q) IgG, IgA and IgM) ELISA kits were from Alpha Diagnostic. The ELISA kit for human circulating immune complexes (C1q-coated plates) was from ALPCO, and the ELISA kit for human IgE was from Mabbiotech. All commercial ELISAs were performed according to the manufacturer's instructions. To measure both human and mouse dsDNA-specific IgE and dsDNA-specific IgG subclasses, dsDNA-coated plates (Calbiotech) were incubated with serial dilutions of serum in PBS containing 10% FCS (Invitrogen). The corresponding horseradish peroxidase-conjugated secondary antibodies were used (FIG. 23). Optical density at 450 nm was measured after tetramethylbenzidine substrate incubation (Invitrogen). Data shown are from 1 in 200 dilution plates (with which the best signal-to-noise ratio was obtained). The same approach was used to measure the amounts of circulating IgE-specific IgGs in subjects and healthy controls, using plates coated with human IgE (Abbiotec) at 2 μg ml$^{-1}$ in PBS.

CICs were precipitated from sera of aged mice as described previously. (Toran, E. J. & Lee, C. M. (1995) *J. Natl. Med. Assoc.* 87, 693-699) Samples were analyzed by SDS-PAGE followed by western blotting with the indicated antibodies (FIG. 23). The LiCor Odyssey System was used to detect signal.

Basophil cultures, basophil detection and measurement of interleukin-4 production. Bone marrow-derived cultured basophils have been previously described. (Charles, N. et al. (2009) *Immunity* 30, 533-543). At day 9 of culture, cells were washed, resuspended at one million cells per ml in medium containing only IL-3 (Peprotech) and incubated overnight at 37° C. Cells were then resuspended in the same medium at five million cells per ml and stimulated as indicated in FIG. 3. For IgE and antigen stimulation, cells were sensitized with 1 μg ml$^{-1}$ of dinitrophenyl-specific IgE for 30 min, washed and then stimulated with 20 ng ml$^{-1}$ of dinitrophenyl-HSA (Sigma). For IgE-immune complex and IgG-immune complex stimulations, IgE- or IgG-containing immune complexes were prepared by incubating either IgE and antibody to mouse IgE or IgG1 and antibody to mouse IgG1 at a 1:2 ratio for 30 min at 37° C. (see FIG. 23). The indicated concentrations of immune complexes (FIG. 3) were then added to the cells for 4 h at 37° C. Two hours before the end of this incubation, 10 μM monensin (Sigma) was added to the cells. Intracellular staining was done as previously described. (Charles, N. et al. (2009) *Immunity* 30, 533-543).

Immunohistochemistry for basophil detection was performed as previously described. (Kepley, C. L. et al. (1995) *J. Immunol.* 154, 6548-6555; McEuen, A. R. et al. (1999) *Lab. Invest.* 79, 27-38).

Statistical Analyses.

For comparisons between two populations, an unpaired two-tailed Student's t test was performed, unless otherwise specified. When three or more populations were compared, a one-way analysis of variance test was first performed, and, if significance was reached (P<0.05), an unpaired two-tailed Student's t test was performed between each compared population, unless otherwise indicated. Statistical analysis was performed with GraphPad Prism 5.01 software.

Mouse Blood

Mice were euthanized by CO$_2$ according to NIH guidelines. Immediately after death, cardiac puncture was done using a 25 G needle, and a minimum of 500 μl of blood was withdrawn in a heparinized tube. Blood samples were then centrifuged at 700×g at 4° C. for 20 min to obtain the plasma. The latter was kept at 20° C. for further analysis. The harvested blood cells were resuspended in 5 ml of ACK lysing buffer (150 mM NH$_4$Cl, 12 mM NaHCO$_3$, 1 mM EDTA, pH 7.4) at room temperature for 3 min, then further incubated for 5 min at 4° C. Subsequently, 10 ml of PBS was added and the sample was centrifuged at 500×g for 5 min. When red blood cells were still present, cells were further incubated in ACK lysing buffer for 5 min at 4° C. and the steps outlined above were repeated until red blood cells were not present. The remaining white blood cells were resuspended in FACS buffer (PBS/1% BSA/0.05% NaN$_3$). Basophils were identified as CD49b$^+$FcεRIα$^+$CD11b$^+$CD117$^-$. B cells were identified as B220$^+$IgM$^+$.

Bone Marrow.

Both femurs were harvested and the bone marrow was flushed out using a syringe containing 3 ml of FACS buffer equipped with a 30 G needle. Recovered cells were centrifuged and red blood cells lysed in 3 ml of ACK lysing buffer for 3 min on ice. Subsequently, 10 ml of PBS was added and the sample was centrifuged (500×g, 5 min). Cells were then stained for FACS analysis. Basophils and total B cells were identified as above. Recirculating B cells in the bone marrow were defined as B220$^{hi}$ IgM$^+$ (an intermediate mean fluorescence intensity is seen in this IgM$^+$ population).

Spleen.

The spleen was harvested and weighed as a measure of splenomegaly. The spleen was then homogenized to a single cell suspension by using tweezers. The cell suspension was centrifuged (500×g, 5 min), and red blood cells were lysed in 5 ml of ACK lysing buffer for 5 min on ice. PBS (20 ml) was added and the sample was again centrifuged (500×g, 5 min). Cells were then resuspended in FACS buffer (10 ml) and filtered on a 40 µm pore diameter cell strainer (BD Biosciences). 1 ml of this cell suspension was used for FACS staining as indicated. Basophils and B cells were identified as above. For the percent of CD11b$^+$ cells in the spleen, the CD11b$^{hi}$ population was gated.

Peritoneum.

Proportion of peritoneal mast cells being mast cells were determined as previously described (Hibbs, M. L. et al. (1995) *Cell* 83, 301-311).

Human Blood Samples.

Blood was harvested in EDTA-coated tubes. 4 ml of blood was used to harvest plasma sample. For this purpose, blood was centrifugated at 600×g for 20 minutes at 4° C. Plasma phase was then harvested, and samples kept at 20° C. until further analysis. For basophils analysis, 10 ml of whole blood were added to 20 ml of ACK lysing buffer and incubated 5 min at room temperature and 5 more minutes on ice. 30 ml of PBS was added, and cells were centrifuged (500×g, 5 min). This step was repeated three times total until no more red blood cells were visible. Cells were then resuspended into 10 ml (original volume) of FACS buffer (PBS/1% BSA/0.05% NaN$_3$). Number of leukocytes per ml and viability were assessed with a ViCell cell counter (Beckman and Coulter). Viability was always over 90%. Cells were then processed for extracellular staining with the indicated surface markers. For basophil absolute counts, basophils were identified as FcεRIα$^+$CD203c$^+$CD123$^+$ CD11b$^+$ cells. For HLA-DR expression analysis, basophils were identified as FcεRI$^+$CD203c$^+$CD11b$^+$. For CD62L expression analysis, basophils were identified as FcεRIα$^+$ CD203c$^+$CD123$^+$.

Histological Analysis for Glomerular Pathological Features in Mice.

Histological analysis for glomerular pathological features included: inflammation, proliferation, crescent formation, and necrosis. A minimum of thirty glomeruli, of at least ten aged mice per genotype, were scored. For each glomerulus, a score from 1 to 5 (1, normal; 2, moderate; 3, severe; 4, severe with crescent formation and 5, necrosis) was used. Scores from each individual mouse were added and averaged to yield the glomerulonephritis score. All pathological assessments were performed in a blinded fashion.

Assessment of Cytokine Content in Mouse Kidney.

For, the kidney was homogenized in 800 µl of PBS containing protease inhibitors (Roche) and centrifuged at 10,000×g for 20 min. Total protein content was determined (Dc protein assay, BioRad) and IL-4 (BD Bioscience), IL-13, IL-6, IL-1β, CCL2, and IFNγ (eBioscience) were measured by ELISA according to the manufacturer's instructions.

Patient's Lupus and Nephritis Activity Assessment.

Lupus activity was assessed by SELENA-SLEDAI (Safety of Estrogens in Lupus Erythematosus National Assessment Systemic Lupus Erythematosus Disease Activity Index) scores[35]. Based on the SLEDAI score, lupus activity was classified as inactive (0), mild (1.0-4.0) and active (>4). Active lupus nephritis was defined by the presence of an active urinary sediment and either a urinary protein creatinine ratio of >1 or immunosuppressive treatment for proliferative lupus nephritis.

Enzyme-Linked Immunosorbant Assays.

For the different immunoglobulin isotypes analysis, anti-mouse IgM, IgA, IgG$_1$, IgG$_{2a}$, IgG$_{2b}$ and IgE ELISA kits were purchased from Bethyl Laboratories.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of treating lupus nephritis in a subject in need thereof, the method comprising administering to the subject an effective amount of an agent that reduces the expression or biological activity of IgE or an IgE receptor in the subject, wherein the agent is an antibody or fragment thereof that selectively binds IgE and is an IgE antagonist and effectuates the amelioration of lupus nephritis.

2. The method of claim 1, wherein the method reduces at least one of: the level of autoreactive IgEs, the level of circulating immune complexes, basophil activation, or combinations thereof.

3. The method of claim 1, wherein the subject has elevated IgE levels.

4. The method of claim 1, wherein the antibody is a monoclonal antibody.

5. The method of claim 4, wherein the monoclonal antibody is a humanized monoclonal antibody.

6. The method of claim 1, wherein the method further comprises administering to the subject an agent selected from the group consisting of nonsteroidal anti-inflammatory drugs (NSAIDs), hydroxychloroquine, corticosteroids, cyclophosphamide, azthioprine, methotrexate, mycophenolate, belimumab, dehydroepiandrosterone, and rituximab.

7. A method of treating lupus nephritis in a subject in need thereof, the method comprising administering to the subject an effective amount of an agent that decreases the number or activity of basophils or that reduces basophil activation in the subject, wherein the agent is an antibody or fragment thereof that selectively binds IgE and is an IgE antagonist and effectuates the amelioration of lupus nephritis.

8. The method of claim 7, wherein the method reduces levels of one or more of CD203c expression, CD62L, and HLA-DR in said subject.

9. The method of claim 7, wherein the antibody is a monoclonal antibody.

10. The method of claim 9, wherein the monoclonal antibody is a humanized monoclonal antibody.

* * * * *